US010729179B2

(12) United States Patent
Atkins et al.

(10) Patent No.: US 10,729,179 B2
(45) Date of Patent: Aug. 4, 2020

(54) ANEMOMETRIC-ASSISTED CONTROL OF A VAPORIZER

(71) Applicant: JUUL LABS, INC., San Francisco, CA (US)

(72) Inventors: Ariel Atkins, San Francisco, CA (US); Adam Bowen, San Francisco, CA (US); Alexander J. Gould, San Francisco, CA (US)

(73) Assignee: Juul Labs, Inc., San Francisco, CA (US)

(*) Notice: Subject to any disclaimer, the term of this patent is extended or adjusted under 35 U.S.C. 154(b) by 37 days.

(21) Appl. No.: 15/669,768

(22) Filed: Aug. 4, 2017

(65) Prior Publication Data
US 2018/0042306 A1 Feb. 15, 2018

Related U.S. Application Data

(60) Provisional application No. 62/371,463, filed on Aug. 5, 2016.

(51) Int. Cl.
A24F 47/00 (2020.01)
H05B 1/02 (2006.01)
(Continued)

(52) U.S. Cl.
CPC ......... A24F 47/008 (2013.01); A61M 11/042 (2014.02); A61M 15/06 (2013.01); H05B 1/0297 (2013.01); A61M 2016/0021 (2013.01); A61M 2205/13 (2013.01); A61M 2205/16 (2013.01); A61M 2205/17 (2013.01); A61M 2205/332 (2013.01); A61M 2205/3331 (2013.01); A61M 2205/3368 (2013.01);
(Continued)

(58) Field of Classification Search
CPC .................................................. A24F 47/008
See application file for complete search history.

(56) References Cited

U.S. PATENT DOCUMENTS 9,877,519 B2 * 1/2018 Xiang .................. A24F 47/008
2010/0313901 A1 * 12/2010 Fernando .............. A24F 47/008
131/330

(Continued)

FOREIGN PATENT DOCUMENTS

WO WO-2013060784 A2 5/2013
WO WO-2013098397 A2 7/2013
(Continued)

Primary Examiner — James Harvey
(74) Attorney, Agent, or Firm — Mintz, Levin, Cohn, Ferris, Glovsky and Popeo, P.C.

(57) ABSTRACT

Vaporizer devices and methods for detecting inhalation through a vaporizer using a heating element are provided. A resistive heater of a vaporizer may function as both a heater and as an anemometer to detect inhalation. Alternatively or additionally, a separate resistive heater may be included in an air path through the vaporizer to detect a user inhaling through the vaporizer. A heating control mechanism utilizes the already existing heating element in an anemometric correlation to when the vaporizer is idle and when it is being used (where being used implies the user is taking a puff/inhalation on the vaporizer). Using this information, a controller of the vaporizer accordingly controls heating to the vaporizer as required.

43 Claims, 11 Drawing Sheets

(51) Int. Cl.
*A61M 15/06* (2006.01)
*A61M 11/04* (2006.01)
*A61M 16/00* (2006.01)

(52) U.S. Cl.
CPC . *A61M 2205/3653* (2013.01); *A61M 2205/70* (2013.01); *A61M 2205/702* (2013.01); *A61M 2205/8206* (2013.01)

(56) References Cited

U.S. PATENT DOCUMENTS

| | | |
|---|---|---|
| 2014/0096781 A1 | 4/2014 | Sears et al. |
| 2014/0261495 A1* | 9/2014 | Novak, III ............ A24F 47/008 131/329 |
| 2014/0345631 A1* | 11/2014 | Bowen .................. A24B 15/16 131/328 |
| 2017/0027226 A1* | 2/2017 | Mironov ............... A24F 47/008 |
| 2017/0135406 A1* | 5/2017 | Reevell ................. A24F 47/008 |
| 2018/0027883 A1* | 2/2018 | Zuber ................... A24F 47/008 |
| 2018/0042306 A1* | 2/2018 | Atkins .................. A61M 15/06 |
| 2018/0043114 A1 | 2/2018 | Bowen et al. |
| 2018/0056015 A1 | 3/2018 | Shwadchuck |
| 2018/0116292 A1* | 5/2018 | Atkins .................. A61M 15/06 |

FOREIGN PATENT DOCUMENTS

| WO | WO-2016009202 A1 | 1/2016 |
|---|---|---|
| WO | WO-2016030661 A1 | 3/2016 |
| WO | WO-2016147188 A1 | 9/2016 |

\* cited by examiner

FIG. 5

ANEMOMETRIC-ASSISTED CONTROL OF A VAPORIZER

CROSS REFERENCE TO RELATED APPLICATIONS

This current application claims priority to U.S. Provisional Patent Application No. 62/371,463, filed Aug. 5, 2016, the disclosure of which is incorporated herein by reference in its entirety.

BACKGROUND

Electronic vaporization apparatuses, including electronic cigarettes, e-cigs, vaporization apparatuses, etc. (referred to herein as "vaporizers" or "vaporizer devices"), have gained popularity in recent years. One reason for the popularity is that vaporizers produce less carcinogens than regular cigarettes and/or other inhalable products when burned and smoked.

Electronic cigarettes are typically battery-powered vaporizers that simulate the feeling of smoking, but without actually burning tobacco. Instead of cigarette smoke, the user inhales an aerosol, commonly called vapor, typically released by a heating element that atomizes a vaporizable material, which may be a liquid solution, a solid, a wax, or a combination of these materials. A user may activate the vaporizer by taking a puff or pressing a button. Some vaporizers look like traditional cigarettes, but they come in many variations.

In many of the electronic cigarettes on the market today, a user-actuated button or user-suction sensor is employed to activate the heating element of the vaporizer. A manual actuation mechanism (e.g. a button, a trigger, or other control that requires a separate user action or input to cause activation of the heating element) for initiating heating may not be desirable in certain situations. For example, requiring use of a button or other manual actuation mechanism may prevent a user from being able to easily synchronize when he or she manually activates the heating and when a puff is taken. Furthermore, if some further user action or input (e.g. a second push of a button, etc.) is required to turn off or otherwise reduce power to the heating element from a vaporization mode, it becomes more likely that the user forgets to cause the heater to turn off, and, as a result, the heater may be left on for a longer period of time than is desirable. Maintaining the heating element at an unnecessarily elevated heating level when airflow is not occurring can lead to scorching of the vaporizable material, as well as a greater level of degradant products in the aerosol to be inhaled. It can also lead to more rapid discharge of a battery or other power source for powering the heating element such that a reduced time between charging may be necessary.

In the case of heating activated by user-caused suction on a vaporizer (e.g. as would be caused by a user "puffing" on the vaporizer or otherwise inhaling to draw air through the vaporizer past the heating element), the heater can be activated when airflow consistent with a user drawing (inhaling into) the mouthpiece of the vaporizer is detected, typically by a pressure sensor or the like. Unfortunately, such user-suction triggered activation is not always reliably implemented due to issues that may arise with commonly used sensors. In at least some vaporizers that utilize user-suction activation of the heating component, a pressure sensor is disposed in communication with the air path. For example, a microphone sensor may be used as the pressure sensor. Such microphone pressure-sensing components are generally quite adaptable for use in vaporizing devices because they tend to be small, very sensitive, and relatively inexpensive. However, they may be less reliable and may break over time. These microphone sensors sense deflection of a fine membrane and output a variance in capacitance. The fine membrane is typically designed to vibrate in the presence of sound and/or pressure waves in the air, and thus will easily deflect under the negative pressure induced by user suction. However, such membranes generally degrade with repeated use and may therefore cause a less reproducible user experience, lose sensitivity to certain puff events, and/or even stop working altogether.

While a microphone-based sensing mechanism can be acceptably functional for controlling heating within a vaporizing device, the longevity of such sensors may be further compromised because they are not designed to function in a vaporizing device environment. Microphone membranes are typically designed to function in a fairly clean and dry environment. In contrast, the environment within or around a vaporizer may be moist, and the membrane may be placed in contact with aerosols, particulates, heat, aqueous and/or non-aqueous liquids, and/or other complicating environmental factors whenever it is in use. Furthermore, over time residue from the vaporized material may deposit onto the membrane. Such residue may saturate the membrane sensor and possibly inhibit membrane deflection altogether, thereby rendering the membrane sensor (and in turn, the heating control of the vaporizing device) inoperable. To mitigate such issues, vaporizer manufacturers have attempted to isolate the microphone from the air path with long and/or circuitous paths. However, these paths can present a design challenge in that they must generally be quite narrow in order to prevent contamination from rapidly reaching the sensor. Unfortunately, the narrow paths can become clogged with viscous material, which can prevent a negative pressure event imparted by a user inhaling or otherwise taking a "puff" on the device from being detected by the microphone. If the material being vaporized is of a low viscosity, it may not prevent the pressure differential from reaching the microphone membrane. However, the fluid may eventually saturate the pressure sensor by capillary action, thereby resulting in reduced or even completely eliminated sensitivity of the sensor.

SUMMARY

Aspects of the current subject matter relate to regulating heat within a vaporizer device.

A heating control approach consistent with implementations of the current subject matter involves monitoring one or more parameters of a heating element configured for heating of a vaporizable material, and making using of the monitored parameters in an anemometric correlation from which it can be determined whether the vaporizer is idle and when it is being used. When a user initiates an inhalation on the mouthpiece of the vaporizer, a greater amount of air passes over the heating element. The rush of air flowing past the heating element when the puff begins causes additional heat loss from the heating element relative to when the air around it is stagnant. This cooling effect of air flowing around and/or past the heating element results in a change of one or more parameters of the heating element. Using information on the change of the one or more parameters, the vaporizer controls, according to aspects described herein, are able to determine if a user has begun and/or ended an inhalation event on the vaporizer and accordingly to control power delivered to the heating element to cause it to vary between at least a first, lower (e.g. standby) temperature and a second, higher (e.g. active or vaporizing) temperature.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to vaporizer devices, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 5 illustrates features of an exemplary vaporizer device consistent with implementations of the current subject matter;

When practical, similar reference numbers denote similar structures, features, or elements.

DETAILED DESCRIPTION

Figure 1A:
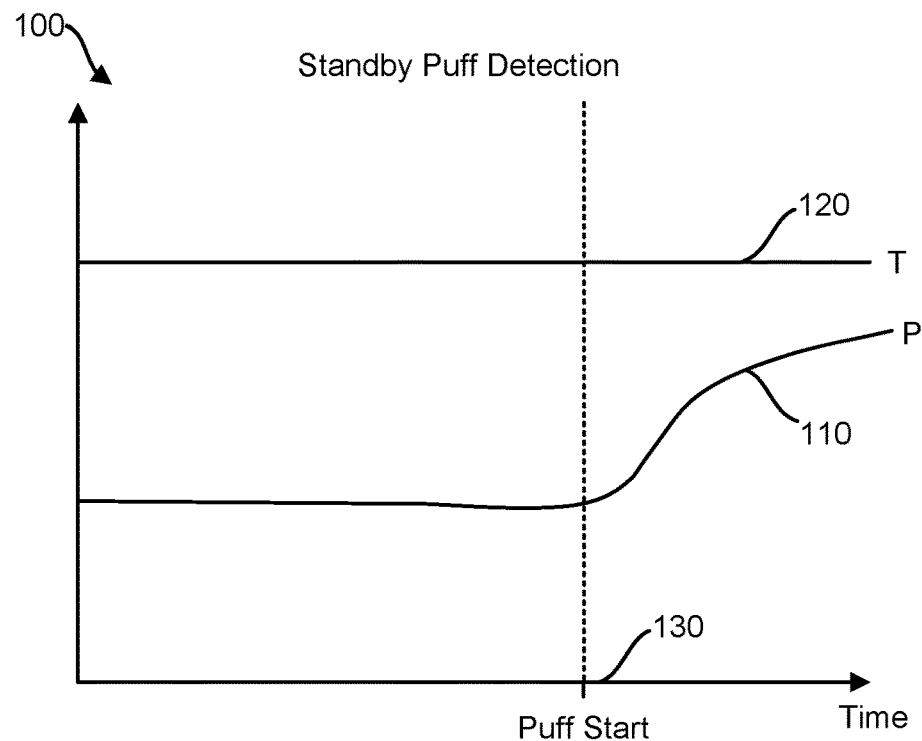
FIGS. 1A and 1B illustrate features relating to detecting a change in power and a change in temperature, respectively, for regulating heat within a vaporizer device, consistent with implementations of the current subject matter.

Implementations of the current subject matter include methods and devices relating to generating a vapor from a vaporizable material and controlling heat delivered to the vaporizable material. The term "vaporizer" is used generically in the following description and refers to a vaporizer device. Examples of vaporizers consistent with implementations of the current subject matter include electronic vaporizers, electronic cigarettes, e-cigarettes, or the like. In general, such vaporizers are often portable, frequently hand-held devices that heat a vaporizable material to provide an inhalable dose of the material. The vaporizable material used with the vaporizers may be a liquid, a gel, a paste, a solid, or any material with any other physical consistency.

A vaporizer having features consistent with certain implementations of the current subject matter includes a heating control mechanism for controlling heating within the vaporizer. A heating control mechanism consistent with implementations of the current subject matter can provide certain advantages, such as being less affected by particulate or residue deposits, as may commonly occur in conventional heating control mechanisms for vaporizers.

In general, a vaporizer having features consistent with certain implementations of the current subject matter includes a device body integrated with or connectable to a mouthpiece, at least one heating element (e.g., a heater such as a resistive heater), a controller (e.g., a microcontroller unit), and a power supply.

The heating element can be configured to deliver thermal energy to a vaporizable material (e.g. via one or more of conductive, convective, and radiative heat transfer) to thereby heat the vaporizable material such that vapors escaping from the vaporizable material may be inhaled by the user through the mouthpiece. Unlike a flow sensor using a pressure sensor (e.g., having a microphone membrane) described above, a vaporizer having features consistent with various possible implementations of the current subject matter may employ a heating element used for vaporizing and/or optionally a second heating element or otherwise heated component of the vaporizer to detect puffing (draw and air flow, resulting from user-created suction on the vaporizer), for example to regulate power being supplied to the vaporizable material according to whether a puff has been detected (or not detected) within a certain time frame.

The heating element may be a resistive heating element that functions also as an anemometer and vaporizes the vaporizable material. Thus, in addition to providing heating to the vaporizable material, the resistive heating element may be used to sense the flow of air as it passes over the heater. In some instances, the heating element may experience a drop in surface temperature and the microcontroller can register the change in its surface temperature as air flowing past it.

As used herein, the terms "anemometer" or "anemometric" refer to systems and methods for measuring air flow and changes in temperature of an anemometer wire element as air flows past it. Typically, hot wire anemometers use a very fine wire (on the order of several micrometers) electrically heated to some temperature above ambient air temperature. Air flowing past the wire cools the wire. As the electrical resistance of most metals is dependent upon the temperature of the metal (tungsten is a popular choice for hot-wires), a relationship can be obtained between the resistance of the wire and the air flow speed. Several ways of implementing this exist, and hot-wire devices can be further classified as CCA (constant current anemometer), CVA (constant voltage anemometer), and/or CTA (constant-temperature anemometer). The voltage output from these anemometers is thus the result of some sort of circuit within the device trying to maintain the specific variable (current, voltage, or temperature) constant, following Ohm's law (V=IR). As described herein, one or more parameters (e.g. an applied current, an applied voltage, a temperature, a resistance, a power required to maintain the heating element at a given temperature, etc.) of a heating element within a vaporizer may be monitored, and a change in such parameters matching a certain predetermined pattern can be interpreted as being indicative of a puff having started and/or stopped such that a temperature at which the heating element is maintained can be varied between at least two different setpoints. For example, when a puff is not detected (and optionally when one has not been detected for a set period of time and/or according to some other criteria), the heating element can be maintained at a first temperature, which can be referred to as a standby temperature in some examples. When a start of a puff is detected (and optionally for some time after the start of the puff), the heating element can be elevated to a second temperature, which can be referred to as a vaporizing or vaporization temperature in some examples. The term "one or more parameters of a heating element" as used herein is intended to refer to either or both of an actual heating element itself, which can be a component of a heating circuit to which power is applied such that electrical resistance of the heating element causes the applied electrical power to be converted to heat, and other components that are part of the heating circuit. Those other components may, in some implementations of the current subject matter, include the power source or power supply, one or more integrated circuits, resistors, capacitors, conductive elements for connecting other components of the heating circuit, a microcontroller or other processor, etc.

The amount of air flow that passes over the heating element may be correlated with usage of the vaporizer. The heating element of the vaporizer described herein may be situated in the air flow path through the vaporizer. This can allow for accurate sensing and measurement of the air flow as well as effective cooling of the heating element.

When a vaporizer is in an unused stated, the amount of air flow over the heating element may be negligible. When the user inhales on the device mouthpiece (e.g. takes a puff), there is generally a significant change in the amount of air flow that passes over the heating element. The change in air flow over the heating element affects the amount of power needed to maintain a certain temperature of the heating element. In the instance where the vaporizer is on or in use, when there is no air flow moving past the heating element, a certain amount of power is needed to maintain a base or standby temperature of the heating element, and if there continues to be no increase in air flow over the heating element, the amount of power needed to maintain a certain temperature reaches some steady state value. When the heating element has been maintained at the standby temperature and there is air flow over the heating element (such as when a user takes a puff on the vaporizer), the additional air flow passing over the heating element cools the heating element by a certain amount. In general, a small amount of air flow passing over the heating element has a smaller effect on the heating element as compared to a greater amount of air flow. This relationship may be pre-programmed into the microcontroller. The change (or drop) in heating element temperature, and/or a change in some other measurable parameter of the heating element such as a current draw, a voltage, a resistance, a power required to maintain a given temperature, etc., may be correlated with the amount of air flow over the heating element, and may be used to discern when a user takes a puff on the vaporizer. In some implementations, the temperature of the heating element is desirably a temperature greater than ambient air temperature (e.g. such that holding the heating element in a steady state at this temperature requires some power delivery from the power source). A heating control mechanism consistent with certain implementations of the current subject matter takes advantage of this feature for controlling heating using components already present in the vaporizer. This approach can be advantageous over conventional vaporizers that utilize additional components, such as pressure sensors, for example because the current implementation is capable of detecting puffing without extra equipment (thereby reducing costs) and without use of a sensor that may be prone to degradation or failure when exposed to environmental factors typical of a vaporizer.

According to some aspects of the current subject matter, the temperature of the heating element when the vaporizer is idle is a pre-set, standby temperature. In general, the standby temperature should not be so hot that it may cause vaporization or degradation of the vaporizable material when the vaporizer is in a standby mode. The standby temperature should also not be too low or close to ambient temperatures because increases in air flow over the heating element would not necessarily cause a proportionate or a measurable drop in temperature of the heating element. In some examples, the standby temperature is between approximately 50 degrees and 70 degrees Celsius.

As noted above, a heating control approach consistent with implementations of the current subject matter can involve monitoring one or more parameters of a heating element configured for heating of a vaporizable material and making using of the monitored parameters in an anemometric correlation from which it can be determined whether the vaporizer is idle (e.g. not being puffed on) and when it is being used (where being used implies the user is taking a puff/inhalation on the vaporizer). When a user initiates an inhalation on the mouthpiece of the vaporizer, a greater amount of air passes over the heating element. In the standby mode, the heating element is maintained at some pre-set temperature greater than ambient temperatures prior to the greater amount of air flow coming into contact with it from a user inhalation. The rush of air flowing past the heating element when the puff begins causes additional heat loss from the heating element relative to when the air around it is stagnant. This cooling effect of air flowing around and/or past the heating element results in a change of one or more parameters of the heating element (as discussed above). Using information on the change of the one or more parameters, the vaporizer controls described herein are able to determine if a user has begun and/or ended an inhalation event (e.g. a puff) on the vaporizer and accordingly to control power delivered to the heating element to cause it to vary between at least a first, lower (e.g. standby) temperature and a second, higher (e.g. active or vaporizing) temperature.

The vaporizer may include a microcontroller configured to receive information on the heating element to determine the state of the vaporizer. The microcontroller may include circuitry, switches, and pre-programed algorithms for responding to the information detected at the heating element. The microcontroller is typically in electrical communication with the heating element as well as the power source, ON/OFF switch, and other electronic components that the vaporizer may include (LED display, sound, etc.).

The microcontroller may be a proportional integral derivative controller (PID). A PID controller calculates an "error" value as the difference between a measured process variable and a desired set-point. One set-point (e.g., a pre-determined value) here is the standby temperature, while the second set-point is the vaporization temperature. The microcontroller may run a PID control loop to energize the heating element and hold it at the standby temperature when the vaporizer is turned on.

FIG. 1A is a graph 100 that illustrates features related to detecting a change in power supplied to the heating element of a vaporizer, consistent with some implementations of the current subject matter. As noted, above, the microcontroller can be configured to periodically measure a parameter (the singular form is used for the remainder of the disclosure for simplicity of discussion, but as noted above, more than one parameter can be used) of the heating element while the vaporizer is in an ON state and in the standby mode at the standby temperature 120. The measured parameter can optionally be a power 110 supplied to the heating element under control of the microcontroller to maintain a constant temperature 120 of the heating element. The microcontroller may be pre-programmed with the knowledge that when the heating element is at the standby temperature, a certain, known amount of power is constantly required to maintain the standby temperature. When the power required to maintain the standby temperature of the heating element exceeds a pre-set value, the microcontroller may register this difference as being correlated with a user taking an inhalation on the vaporizer (e.g., the start of a puff 130). This triggers the microcontroller to send signals to the power supply to increase power input into the heating element to a temperature high enough for vaporizing a vaporizable material. The microcontroller may be configured to compare power required to maintain a certain temperature in the heating element in the presence of temperature changes over the heating element and to increase power to the heating element for reaching vaporization temperatures only when the power needed to maintain the standby heating element temperature exceeds a pre-set value. This comparison may be performed digitally, for example via programming of the microcontroller that causes it to performs operations such as receiving inputs indicative of a current power applied to maintain a setpoint temperature and determining whether the current power applied indicates that a puff has started, or via hardware, for example an integrated circuit or the like that registers a voltage or other signal when a certain preset condition is met. A vaporization temperature to which the heating element is raised when a puff is detected may, in some examples, be in the range of, for example, approximately 100 degrees Celsius to approximately 300 degrees Celsius.

Consistent with some aspects of the current subject matter, the control of the vaporizer's heating element may be established through detecting a function of power rather than merely measuring the power itself. For example, trigger conditions that signify a change in power may include a first derivative of power, a second derivative of power, or some combination thereof. The trigger conditions may be an algorithmic or mathematical relationship to the one or more parameters described above. Control of the heating element may be established by detecting the rate of change of the power being supplied to the heating element (or some other algorithmic or mathematical function) while the vaporizer is at the standby temperature. Similar to the prior example where the vaporizer registers and attempts to maintain the standby temperature or the vaporization temperature of the heating element, the microcontroller may be set to register and read the rate of change of the power that is supplied to the heating element while the vaporizer is in the standby mode and at the standby temperature. The measuring of the rate of change in power may provide a more detailed profile of user inhalation. Typically, when a user begins inhaling on a vaporizer, the air flow across the heating element increases rapidly from zero or near zero to some maximum amount and then decreases rapidly as the user ceases puffing, at which the air flow drops dramatically and becomes close to zero. The change of the air flow may be correlated with a change in power required to maintain a temperature of the heating element. When the air flow increases, the heat loss from the heating element increases and the power needed to maintain the standby temperature goes up. This change in power may follow a complex relationship such that improved detection of the start of a puff may be achieved by monitoring one or more derivatives of the delivered power rather than just the current power.

A power value can be set such that once a pre-set power value to maintain a given standby temperature is exceeded, the microcontroller instructs the power supply to increase power to the heating element so the heating element reaches the vaporization temperature. Alternatively, one or more (e.g., a set of) vaporization mode triggering criteria as described above can be applied to determine whether a puff has started and an increase to the vaporization temperature is needed, thereby resulting in the microcontroller increasing power to the heating element. At an end of an inhalation, the air flow drops and the heat loss from the heating element to flowing air resultantly decreases, such that less power is required to maintain the vaporization temperature. Once the power to maintain the vaporization temperature drops to a pre-set power value, the microcontroller may instruct the power supply to decrease the amount of power sent to the heating element so that the heating element temperature drops to the standby temperature. Alternatively, one or more (e.g., a set of) standby mode triggering criteria as described above can be applied to determine whether a puff has ended and a decrease to the vaporization temperature is needed, thereby resulting in the microcontroller reducing power to the heating element.

In other words, in a power delivery monitoring implementation of the current subject matter, the microcontroller is able to detect changes in the heating element temperature with the heating element at the standby temperature and adjust the power supplied accordingly to match the set-point standby temperature. Once a change in the power required to maintain the standby temperature changes sufficiently (as measured by some combination of an actual power value, a first derivative of power delivered, and/or a second derivative of power delivered matches one or more vaporization mode triggering criteria (e.g. due to user taking an inhalation on the vaporizer)), the microcontroller determines that a puff is occurring and enters a puffing state and increases power to the heating element until the heating element is at the vaporization temperature. With the heating element at the vaporization temperature, the microcontroller is also able to detect changes in the heating element temperature and adjust the power supplied accordingly to match the set-point vaporization temperature. Once a change in the power required to maintain the vaporization temperature changes sufficiently (as measured by some combination of the actual power value, the first derivative of power delivered, and/or the second derivative of power delivered matches one or more (e.g., a set of) standby mode triggering criteria (e.g. due to user taking an inhalation on the vaporizer)), then the microcontroller determines that a puff is no longer occurring, as discussed in more detail below with reference to FIG. 2.

Figure 1B:
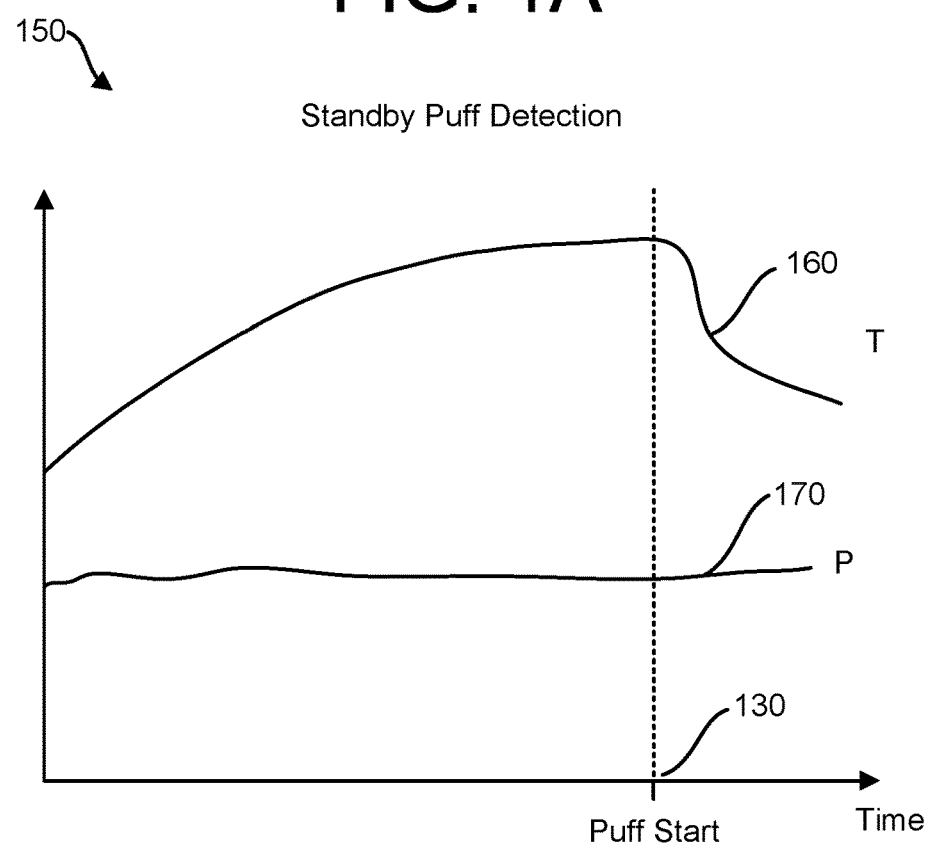

Consistent with some aspects of the current subject matter, and as represented in graph 150 of FIG. 1B, the amount of heat and the timing for heating may be controlled based upon maintaining a constant or near constant power level 170 supplied to the heating element and detecting changes in temperature 160. In this case, a constant power 170 is delivered to the heating element and changes in the heating element temperature 160 (or, alternatively, the temperature of some other component that varies in temperature with changes in airflow) are monitored. The microcontroller can monitor (e.g. continuously, every few seconds, with some other periodicity, etc.) the temperature 160 of the heating element to determine whether the state of the vaporizer needs to be changed. Alternatively, a function of temperature, such as a change in temperature, a first and/or second derivative of temperature, may be monitored. As the amount of air flow passing over the heating element increases due to a user taking an inhalation, the temperature of the heating element decreases. Once the temperature difference between the temperature when there is no significant amount of air flow and when there is an inhalation and air flow over the heating element exceeds a pre-set temperature differential (e.g., a puff start 130), the microcontroller instructs the power supply to increase power to the heating element for reaching the vaporization temperature. The microcontroller continues to measure the temperature (or a function of the temperature) of the heating element when it is at the vaporization temperature as the power supply continues to provide a constant vaporization power level to the heating element. The vaporization temperature may fluctuate slightly due to the change in air flow over the heating element. Once the change in temperature between what may be considered a reference temperature value for vaporization (when there is little to no flow over the heating element during vaporization) and the measured vaporization temperature is negligible, the microcontroller may signal to the power supply to decrease power being supplied to the heating element so that the standby temperature is achieved.

In other words, in a temperature-monitoring implementation of the current subject matter, the microcontroller maintains a constant power delivery level to the heating element with the vaporizer in the standby mode and is able to detect changes in the heating element temperature. When some combination of an actual temperature, a first derivative of temperature, and/or a second derivative of temperature matches one or more vaporization mode triggering criteria, the microcontroller determines that a puff is occurring and enters a puffing state in which power to the heating element is increased to a second power level sufficient to cause the heating element to reach the vaporization temperature. With the heating element at the vaporization temperature, the microcontroller maintains the second power delivery level and is able to detect changes in the heating element temperature. When some combination of an actual temperature, a first derivative of temperature, and/or a second derivative of temperature matches one or more standby mode triggering criteria, the microcontroller determines that a puff is not occurring and enters a standby state in which power to the heating element is decreased to the first power level sufficient to cause the heating element to return to the standby temperature.

In some implementations of the current subject matter, the microcontroller may be configured to detect resistance within the heating element while a constant power is supplied. Resistance may be used as an indicator of temperature in that the resistance of the heating element is a function of temperature. Similarly, changes in resistance of the heating element (and/or changes in one or more rates of change such as the first derivative, second derivative, etc. of resistance) may be measured and correlated with different states of the vaporizer (e.g. standby mode or vaporization mode). In still other implementations of the current subject matter, a change in voltage or current needed to maintain a given temperature can be used as an indicator of power or temperature of the heating element and/or some other component exposed to air flow. These parameters and/or changes in one or more rates of change (e.g. first or second or other derivatives) of such parameters may be monitored and compared to triggering conditions for indicating start of a puff (and therefore a need to switch to vaporization mode) and/or end of a puff (and therefore a need to switch to standby mode).

Figure 2:
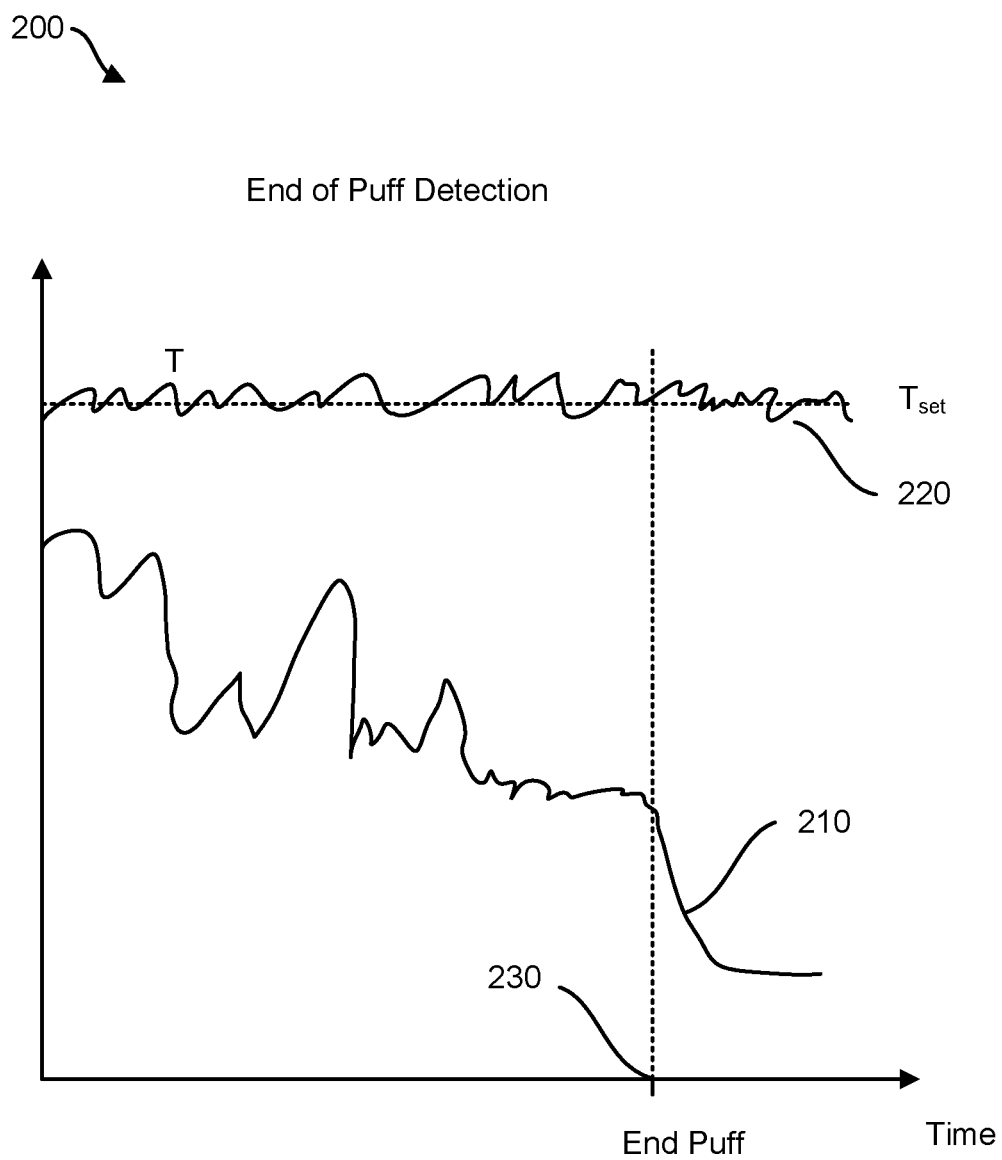
FIG. 2 illustrates features relating to detecting an end of an inhalation by a user of a vaporizer device, consistent with implementations of the current subject matter.

FIG. 2 is a graph 200 that represents detection of an end of an inhalation in a power delivery monitoring implementation of the current subject matter. Once the heating element is at the vaporization temperature, the microcontroller continues to sustain the power being supplied to the heating element for maintaining the vaporization temperature 220 (which may have slight variations and/or fluctuations) until the microcontroller detects that the amount of power 210 needed to maintain the power of the heating element decreases below a second pre-set power value, as represented in the graph 200 of FIG. 2. As with the detection of the start of a puff via comparison of one or more parameters (which can include one or more derivatives of such parameters) with one or more vaporization mode triggering criteria, an end of a puff can be detected via comparison of one or more parameters (which can include one or more derivatives of such parameters) with one or more standby mode triggering criteria. For example, a drop in needed power to the heating element may serve as an indicator that not as much power is needed at the heating element for maintaining the vaporization temperature, which may be correlated with less air flow over the heating element causing heat losses at the heating element. Less air flow over the heating element occurs when the user has completed or nearly completed an inhalation on the vaporizer (e.g., the end of the puff 230). Once the power level needed to maintain the vaporization temperature falls to the second pre-set power level, then the microcontroller can instruct the power supply to decrease power to the heating element to the level for maintaining the standby temperature. In some implementations of the current subject matter, a more complex analysis can be performed involving more than the current value of a parameter such a power required. For example, when some combination, possibly including one or more of an actual power value, a first derivative of power delivered, and/or a second derivative of power delivered matches one or more standby mode triggering criteria (e.g. due to user ceasing an inhalation on the vaporizer), the microcontroller determines that a puff has stopped and enters a standby state in which power to the heating element is decreased until the heating element is at the standby temperature. The more complex analysis, possibly involving a first and/or second derivative of power delivered, may more accurately represent a detection of a change of state of a vaporize. A similar analysis (not illustrated) can be performed for a constant power delivery implementation of the current subject matter as noted above.

Behavior of a vaporizer in cases such as a subsequent puff during a cooling phase before the heating element reaches its standby temperature (e.g., initiation of an inhalation after turning on the vaporizer but before the heating element has reached the standby temperature) or a premature cessation of inhalation while the microcontroller is causing the heating element to heat from the standby temperature to the vaporization temperature, can be desirably improved by use of one or more vaporization mode triggering criteria and one or more vaporization mode triggering criteria that include one or more derivatives of the monitored parameters.

Figure 3:
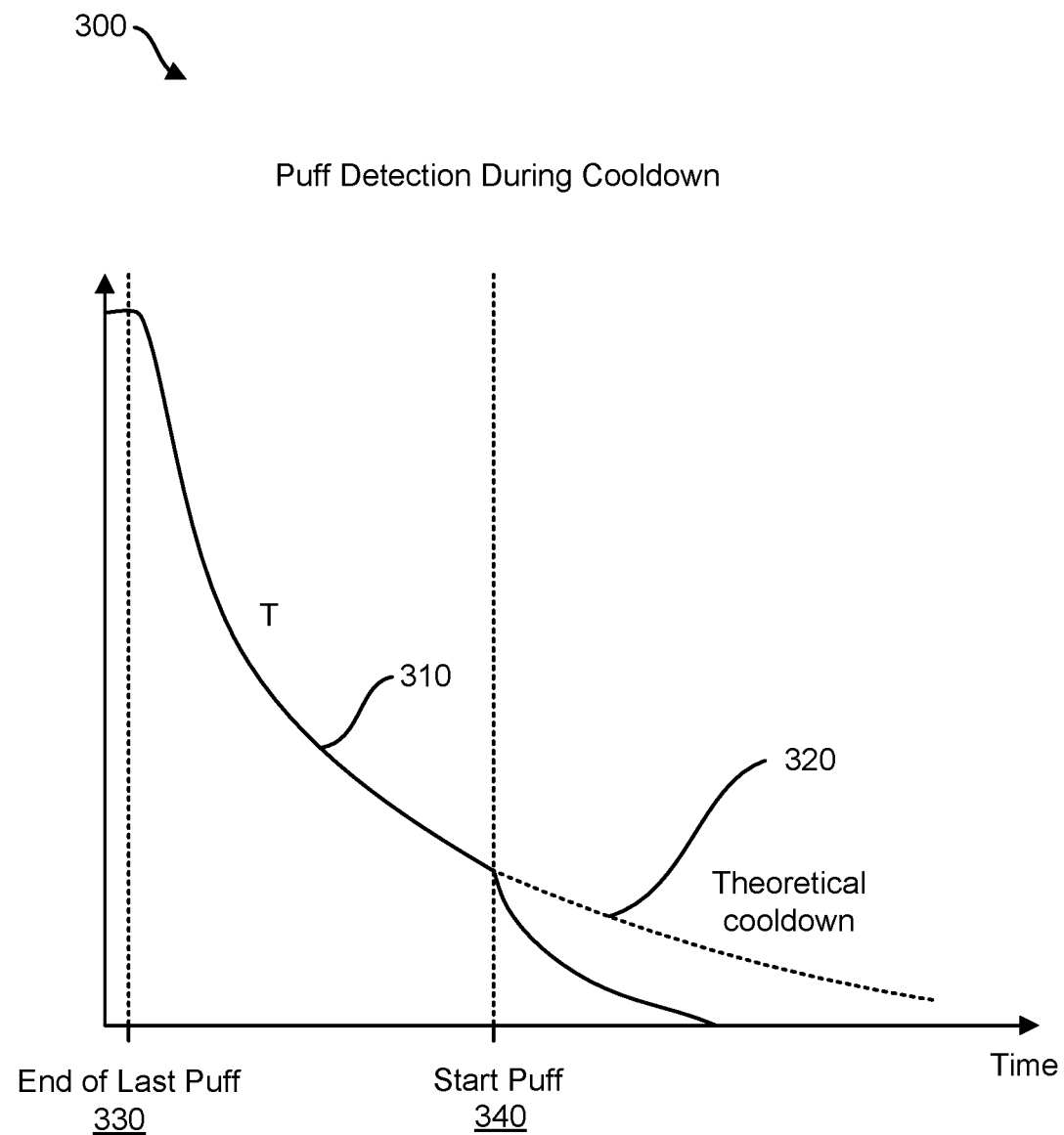
FIG. 3 illustrates temperature features when an inhalation is detected during cooldown of a vaporizer device, consistent with implementations of the current subject matter.

For example, with reference to FIG. 3, graph 300 illustrates temperature features when an inhalation is detected during cooldown. In the graph 300, an end of last puff is represented by point 330, a start of puff by point 340, and a theoretical cooldown curve by curve 320. Once the power requirement falls below a certain pre-determined value, the microcontroller detects the end of the puff 330 and begins to decrease or shut off completely power to the heating element until the standby temperature is reached. The microcontroller may measure the rate of cooling represented by curve 310. In the case when a user ceases an inhalation, sending the device into a cooling phase in which power to the heating element is decreased (or even shut off), but then initiates a subsequent inhalation before the standby temperature has been reached again, the microcontroller is still capable of determining that a next puff has started based on monitoring of one or more derivatives to identify that the actual cooling profile is faster than the theoretical cooldown curve 320.

In another example, a user may initiate an inhalation after turning on the vaporizer but before the heating element has reached the standby temperature. In such a case, the microcontroller may be directed to detect the rate of cooling across the heating element. Where the rate of cooling exceeds a pre-programmed value, the microcontroller directs the power supply to increase power to the heating element so that the heating element can quickly reach the vaporization temperature.

Figure 4:
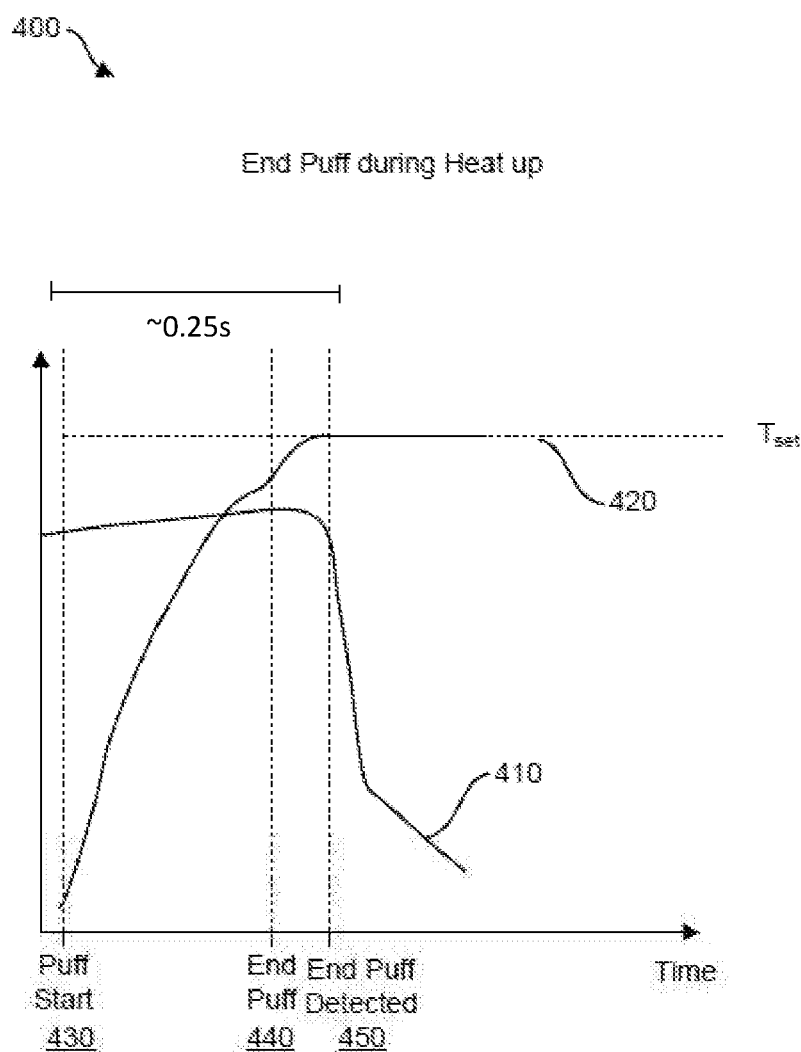
FIG. 4 illustrates temperature and power features relating to detecting an end of an inhalation by a user during heat-up of a vaporizer device, consistent with implementations of the current subject matter.

As represented in graph 400 of FIG. 4 (where a puff start is represented by point 430, a puff end by point 440, and a puff end detected by point 450), a user may stop midway (440) while inhaling on the vaporizer while the heating element is being brought up to the vaporization temperature. In that case, the air flow past the heating element goes from being high enough to trigger and sustain power 410 for reaching and maintaining the vaporization temperature ($T_{set}$ 420) to practically no air flow past the heating element. In one example, the microcontroller may allow the heating element to reach the vaporization temperature (if the heating element had not reached it prior to the stop in air flow) and, similar to what occurs when inhalation is not abruptly halted (see FIG. 2), will ramp down the power sent to the heating element once the amount of power required to maintain the vaporization temperature falls below a pre-determined threshold value. In other examples, the microcontroller may be used to sense the rate at which power is being drawn to either bring the heating element to the vaporization temperature or to maintain the vaporization temperature and immediately decrease power to only maintain the vaporization temperature at the standby temperature. In the latter case, the microcontroller does not necessarily wait until the change in temperature or power has dropped past a pre-determined level prior to decreasing the power to a level for sustaining the standby temperature.

Vaporizers having features consistent with certain implementations described herein may have a quick response time for increasing or decreasing power to the heating element. In general, the time for achieving the standby temperature may be less than a couple of seconds. The time for reaching the vaporization temperature once the pre-determined threshold power or threshold change in temperature is reached may be quick (e.g., less than 30 seconds, less than 20 seconds, less than 10 seconds, less than 5 seconds, less than 3 seconds, less than 2 seconds, less than 1 second, etc.)

As mentioned, vaporizers having features consistent with certain implementations described herein may include an ON/OFF switch. An ON/OFF switch may provide clear signal to the microcontroller that the vaporizer should be placed in the standby mode. In other instances, the vaporizer may include an accelerometer for determining when the device should be placed in the standby mode. Based on the motions that the accelerometer detects as compared to a reference accelerometric measurement, the microcontroller predicts when a user may be intending to use the vaporizer. An accelerometer may be programmed to sense certain types of motions associated with use of the vaporizer, or may be programmed for detecting a certain motion or combination of motions that indicate the user intends to use the vaporizer (e.g., spinning the vaporizer or other deliberate motion).

Because use of an accelerometer for determining when the vaporizer should be placed in the standby mode based on motion sensed may potentially have difficulty distinguishing general movement of the vaporizer with movement that is associated with a user wishing to initiate usage of the vaporizer, it may be advantageous to couple the presence of the accelerometer with an alternative sensing mechanism or to utilize an alternative sensing mechanism. In some instances, the additional mode of sensing a user's intent to use the vaporizer may be by way of capacitive sensing, lip sensing, timing, touch sensing, or any combination thereof.

In some aspects of the current subject matter, a capacitive sensing mechanism may be included in the vaporizer in conjunction with an accelerometer or by itself. A capacitive sensing mechanism may be disposed in or around the mouthpiece of the vaporizer. The capacitive sensing mechanism may be used to determine if a user's lips are touching the mouthpiece. The capacitive sensing mechanism is able to distinguish between a user's lips pressing against it as compared to other types of dermal contact. When the capacitive sensing mechanism detects presence of the user's lip, it signals to the microcontroller to turn the vaporizer ON and also to place the device in a standby mode. In examples where the vaporizer includes an ON/OFF switch, the capacitive sensing mechanism may be used to aid with triggering the microcontroller to bring the heating element up to the standby temperature. In some examples, once the capacitive sensing mechanism senses the presence of the user's lip, the microcontroller may signal to the power supply to quickly provide power to heat up the heating element such that the anemometric-related sensing capabilities of the vaporizer are employed as described above.

In some aspects consistent with certain implementations of the current subject matter, the heating element continuously heats at the standby temperature when the vaporizer is switched to an ON state. In general, the heating may only stop heating when the vaporizer is in an OFF state. In most instances, the amount of power needed to maintain the standby temperature is only a few milliWatts and thus having the vaporizer at the standby temperature is not a large drain on the power source.

In general, the heating element may be a resistive heating element that is able to make anemometric correlations between the air flow over the heating element and a change in temperature and power required to maintain that temperature despite air flow cooling down the heating element. The heating element may be placed transverse to the air flow through the vaporizer in order to most accurately correlate air flow (due to user inhalation) with the power required to maintain a pre-determined temperature.

Figure 5:
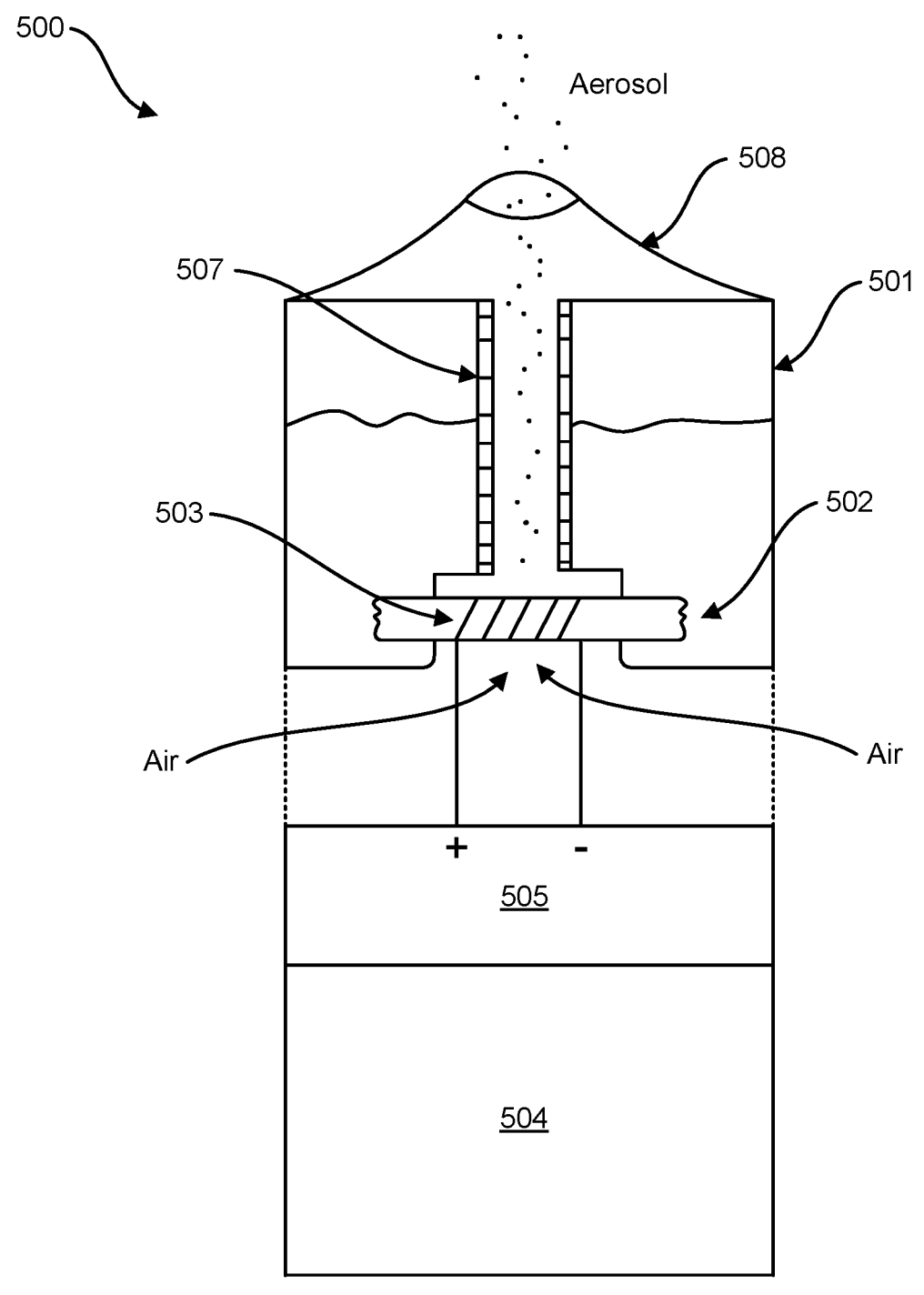

FIG. 5 illustrates features of an exemplary vaporizer device 500 consistent with implementations of the current subject matter. While vaporizer 500 typically includes a cover, FIG. 5 is shown with the cover removed in order to better display the internal components of the vaporizer 500. The vaporizer 500 includes a mouthpiece 508 disposed on the proximal end of the vaporizer 500. A heating element 503 is also contained within the vaporizer 500, where the heating element 503 is in electrical contact with a microcontroller 505. The vaporizer 500 also includes a power supply 504 that is in electrical communication with both the microcontroller 505 and the heating element 503. In this example, the heating element 503 is coiled around a wick 502, while in other examples, the heating element may be in other configurations adapted to heat a vaporizable material. In general, the heating element 503 is in thermal contact or communication with the wick 502, and the wick 502 may be saturated with a vaporizable fluid containing an active compound or substance. In other examples, the wick 502 merely has to be in contact with the heating element 503 such that the vaporizable materials held within the wick 502 may vaporize when the heating element 503 is at the vaporization temperature.

The vaporizer 500 may also include a reservoir 501 for retaining a vaporizable material as shown in FIG. 5. In this example, the wick 502 is in fluid communication with the liquid retained with the reservoir 501 such that as the vaporizable material is vaporized, the wick 502 is able to draw more vaporizable material into it via capillary action and diffusion. In some cases, the fluid reservoir 501 may be removable from the rest of the vaporizer 500 while in other cases, the fluid reservoir 501 may be permanently disposed within the vaporizer 500. In yet other examples, the vaporizer may lack a fluid containing reservoir all together and the wicks may be disposable and pre-loaded with vaporizable material. The advantage of having a wick that may be replaced each time after all the vaporizable material is gone is that there is no leftover residue from each prior vaporization that over time may become harmful.

A defined airflow path 507 may be situated through the vaporizer 500 for ensuring that the air flow flows transversely over the heating element 503 for accurate control of the heating within the vaporizer 500.

When a user takes an inhalation from the vaporizer, air flows to the user's mouth delivering a vaporized material or an aerosol. The vaporizer generally includes at least one vent for bringing in air flow. The air flow path is pre-defined within the vaporizer. The vent is typically disposed at a distal end of the vaporizer such that when the user takes a draw on the vaporizer, air will enter the device and flow over the heating element for providing a way of delivering the vaporized material to the user and for regulating the amount of power supplied to the heating element. In some examples, the at least one vent may further include an air flow regulator or valve for controlling the maximum amount of air flow that may flow to the heating element. In other examples, the at least one vent may further include filter to minimize environment particulate from entering the vaporizer and thus lessen the deposit of outside particulate onto the inner surfaces of the vaporizer over time.

The vaporizer may include channels that aid with directing air flow through the device, over the heating element and vaporized material to be then delivered to the user through the mouthpiece. The channels within the device ensure that a direct flow of air comes into contact with the heating element. The air flow may flow transversely over the heating element to provide accurate correlation between air flow and change in temperature of the heating element as well as more efficient vaporization.

The wick may be composed of a material that is able to absorb a fluid vaporizable material. The wick, through natural capillary action and diffusion, draws fluid from a reservoir containing wetted materials. As the vaporizable material is vaporized due to energy transferred from the heating element, and removed from the wick, more vaporizable material may be drawn into the wick until the vaporizable material is depleted from the reservoir. In some examples, the wick is composed of naturally-derived fibers such as cotton, hemp, bamboo, coconut or man-made materials such as silica fibers, ceramic, metal mesh, and so forth. In some instances, the wick may be for one time use only and need to be replaced after all the vaporizable material is depleted.

The heating element may be in electrical communication with the microcontroller and power supply through connected circuitry. In some instances, the vaporizer may be separable into two pieces where each of the two pieces includes portions of the circuitry for electrically connecting the heating element to the microcontroller and power supply. When the two parts of the vaporizer are connected, the circuitry forms a complete circuit and power may be delivered to the heating element.

The heating element may be a resistive heating element. The heating element may be a wire that is wound into a coil of a fixed diameter for accepting a wick. The heating element may be composed of a platinum wire, tungsten wire, or other suitable material that does not degrade or off-gas at high temperatures. The heating element typically is able to heat at a temperature range of 30 degrees Celsius up to 500 degrees Celsius. In some examples of the vaporizer, it may be possible for the user to set the vaporization temperature from a selection of vaporization temperatures. Having different vaporization temperatures may be useful as different vaporizable materials or compositions vaporize optimally at different temperatures. What vaporization temperature the device functions at may be indicated on the vaporizer (e.g., different color light display).

In general, the power supply may be a battery. The power supply may be rechargeable. Indicators on the vaporizer may be used to indicate if the battery requires recharging and when the battery is fully charged.

Figure 6:
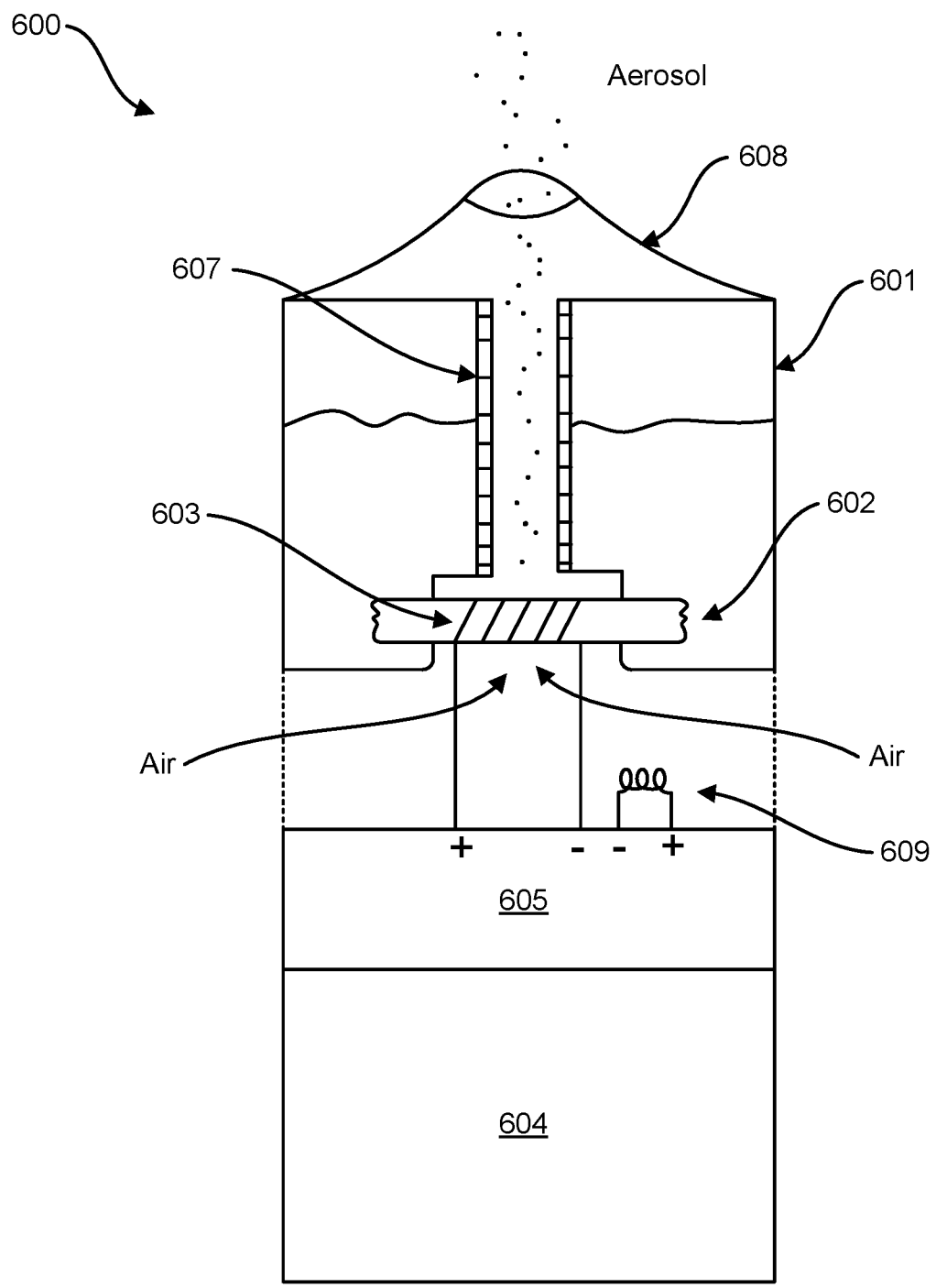
FIG. 6 illustrates features of an additional exemplary vaporizer device consistent with implementations of the current subject matter.

FIG. 6 illustrates features of an additional exemplary vaporizer device 600 consistent with implementations of the current subject matter. The vaporizer 600 may have a second coil 609, separate from the primary heating element 603 as shown in FIG. 6. The second coil 609 may function as an anemometer for controlling power supplied to the heating element 603, consistent with implementations of the current subject matter. The second coil 609, while it is able to heat up, does not provide the heat required to vaporize; vaporization is provided by the first and primary heating element 603. Similar to the vaporizer 500, this vaporizer 600 has generally three states: an OFF state, an ON/Standby state, and an ON/vaporization state. Similar to device 500, the vaporizer 600 includes a microcontroller 605 for controlling communication, inputs and outputs between it, the first heating element 603, the second coil 609, and the power supply 604. In addition, the vaporizer 600 may include a reservoir 601 for retaining vaporizable fluid, a wick 602, as well as a mouthpiece 608. In addition, there is a defined airflow path 607 through the vaporizer 600 for ensuring that the air flow flows transversely over the first heating element 603 and the second coil 609 for accurate control of the heating within the vaporizer 600. In some instances, it may be more important that the air flows transversely over the second coil 609 than the first element 603 because in this alternative design, the second coil 609 measures the air flow, changes to the temperature due to air flow, and the rates of air flow change for controlling the power delivered to the first heating element 603. If air flow travels over the second coil 609 in a non-transverse path, there may be inaccuracies in the flow rate detected that may lead to inaccuracies in determining the effect on temperature that ultimately may lead to not enough or too much power being delivered to the heating element 603.

Like vaporizer 500, the vaporizer 600 enters into a standby mode when the vaporizer 600 is turned on. The microcontroller 604 directly signals the heating element 603 and the second coil 609 to heat to a standby temperature. In some instances, only the second coil 609 is heated to the standby temperature while the heating element 603 remains at ambient temperature. Similarly, the standby temperature is a temperature above ambient temperature and may be anywhere in the range of, for example, 50 and 70 degrees Celsius. The microcontroller 604 maintains the standby temperature at the heating element 603 as long as the vaporizer 600 is on. The microcontroller 604 also periodically measures the power needed to maintain the standby temperature at the second coil 609.

When the user takes an inhalation on the mouthpiece 608, the air flow over the second coil 609 increases and lowers the temperature of the second coil 609 such that more power is required to maintain the standby temperature at the second coil 609. Once the power required to maintain the standby temperature at the second coil 609 exceeds a pre-set power value, then the microcontroller 604 presumes that the user is taking an inhalation at the mouthpiece and initiates heating of the heating element 603 to bring the temperature of the heating element 603 up to the vaporization temperature. The temperature of the second coil 609 may be maintained at the standby temperature during the time that the heating element 603 is being brought up to the vaporization temperature and when the vaporization temperature is being maintained at the heating element 603. The microcontroller 604 continues to send sufficient power to the heating element 603 for maintaining the vaporization temperature until the amount of energy for maintaining the standby temperature of the second coil 609 returns to a value that correlates with no air flow or minimal air flow over the second coil 609. This condition corresponds to the user ending puffing or inhaling on the device. At that point, the microcontroller 604 signals the power supply to cease sending power to the heating element 603 and allows the heating element to reach either the standby temperature or ambient temperatures.

In some instances, the user may suddenly stop inhalation in mid-inhalation. In this scenario, the vaporizer may be in two possible sub-states. In the first, the heating element has not reached the vaporization temperature, while in the second, the heating element is at the vaporization temperature. In both, when the amount of energy required to maintain the standby temperature of the second coil drops below a certain pre-set power value, the microcontroller signals the power supply to stop supplying power to the heating element and allows the heating element to cool to either the standby temperature or an ambient temperature. In other examples, when the vaporizer goes from a standby state to a puff state, the second coil's temperature may also be increased to the vaporization temperature along with the heating element. In the latter case, the power needed to sustain the vaporization temperature will decrease when the power for maintaining the vaporization temperature drops below a pre-set power value (this occurring at the end of an inhalation when little to no air is being flowed over the second coil).

In other instances, the user may initiate an inhalation while the vaporizer is in a cooling phase. In this scenario, upon detecting that the rate of decrease of the heating element temperature or the second coil temperature is greater than a pre-set value, the microcontroller may override the cooling phase and switch back to a heating cycle to increase the temperature back to the vaporization temperature.

The vaporizer 600 shown in FIG. 6 functions similarly as the vaporizer 500 of FIG. 5 except for the addition of the second coil 609. An advantage of the implementation of the vaporizer 600 is that the second coil, because it is downstream of the heating element and the vaporizable material, for most instances, does not come into contact with the vaporizable material or the vapors that result from heating. Thus, over time there is much less likelihood that residue from the vaporizable material will deposit on the second coil wire and negatively affect the heating control and functionality of the vaporizer.

Figure 7:
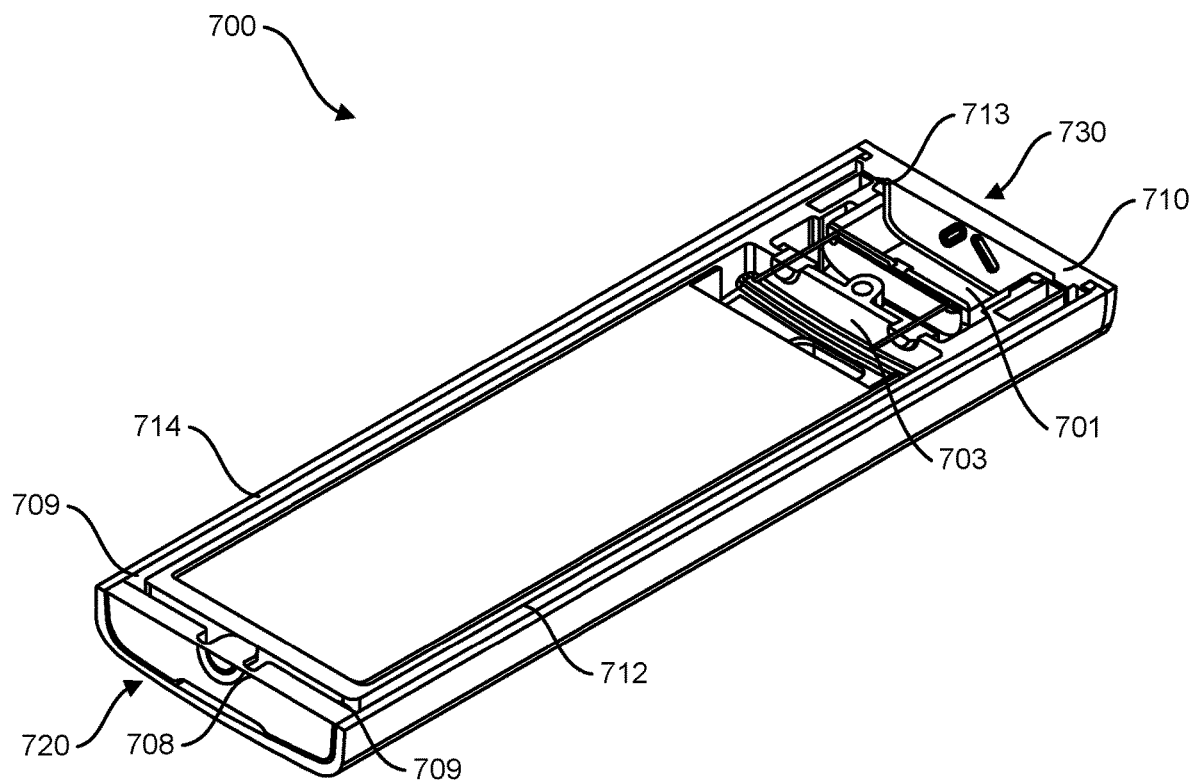
FIG. 7 illustrates features of an another exemplary vaporizer device consistent with implementations of the current subject matter.

Consistent with some implementations of the current subject matter, the vaporizer may be configured to vaporize a solid material (e.g. loose leaf type sample). Vaporizers that are adapted for vaporizing a solid sample may have an oven instead of a wick or wicking material in thermal contact with the heating element, an example of which is illustrated in a cross-sectional view in FIG. 7. Vaporizer 700 includes, near (e.g., nearly adjacent or adjacent) a bottom end 730, an internal oven 701 with a surrounding oven housing 713. A lid 710 mates or otherwise attaches to an outer housing 714 at the bottom end 730. A mouthpiece 708 mates or otherwise attaches to the outer housing 714 at a top end 720. Internal to the outer housing 714 is a structural housing component 712. One or more internal side slots or channels 709 are formed between and extend along the lengths of outer side walls of the structural housing component 712 and inner side walls of the outer housing 714. The internal side channel 709 extends from the oven 701 to the mouthpiece 708, providing a cooling pathway for vaporizable material to be inhaled by a user. Variations of the vaporizer 700 with an oven 701 may be adapted for use with some aspects of the current subject matter.

A heating element 703 is in electronic communication with a microcontroller and power supply. The heating element 703 may be an arrangement of wire, a heating plate, or any other suitable heater for increasing the energy input to the oven 701 for vaporizing the vaporizable material. Similar to the vaporizers having a wick configuration, the vaporizer 700 for vaporizing solid materials may have anemometric controls to regulate heating. The microcontroller contained within is able to determine which state the device should be in (e.g., standby or vaporization state) and when to switch from one to another and then back. The shift from one state to the other is similarly based upon periodically measuring the change in power (or a function thereof) supplied to the heating element against some pre-set power value. The shift in states may also be based upon periodically measuring fluctuations in the temperature (or a function thereof) against a pre-determined variance for the temperature such that if the measured temperature deviation is greater than the pre-set variance, this indicates that a user is taking a puff on the vaporizer; and if the deviation drops to or below the pre-set variance, this indicates that the user is no longer inhaling on the vaporizer. In some other examples, the microcontroller may periodically sample the rate of change in the temperature or power of the heating element against a pre-set rate of change values where if the rate of change in temperature or power exceeds some pre-set value, this serves as an indicator that the user is puffing on the vaporizer; and if the temperature or power rate of change drops to near or at zero, then this serves as an indicator that the user stopping inhalation on the vaporizer.

Apparatuses including an oven in thermal contact with the heating element (such as the vaporizer 700) may be configured to have a sufficiently low thermal mass such that when a user takes an inhalation on the vaporizer, this in turn results in a temperature drop at the heating element or surface. If a typical inhalation has little or no effect on the temperature of the heating element (e.g., thermal mass is too large), then this advantageous feature of anemometric regulation of the heating element may not be effectively used to regulate power and heating of the heating element. In order for the heating element to have low thermal mass, the oven is adapted to be effectively heated by a heating element having low thermal mass. The physical requirements of the heating element affect the oven dimensions and features.

As mentioned earlier, the vaporizers described herein may include a capacitive sensor for determining when a user may begin taking an inhalation on the vaporizer. The capacitive sensor may be located in and around the mouthpiece where when the user presses his or her mouth against the capacitive sensor, the microcontroller instructs the power supply to send more power to the heating element. The capacitive sensor may be used in conjunction with the anemometric determination of when the user is beginning inhalation on the vaporizer.

In some implementations of the current subject matter, the anemometric determination may be used by the microcontroller as a diagnostic tool as a check on whether one or more other sensors are operating correctly. For example, in a vaporizer with a pressure sensor as a primary sensor that causes the heating of a heating element to be activated based upon detecting airflow consistent with a user drawing the mouthpiece of the vaporizer (e.g., user-suction triggered activation), the anemometric sensing approach consistent with implementations of the current subject matter can be used as a verification to confirm if the pressure sensor is properly working. For example, if a user of such a vaporizer with a pressure sensor, suspects a heating problem (e.g., when puffing on the vaporizer, the vaporizer is not heating), the user may turn on a diagnostic mode by performing some predetermined action (e.g., shaking the device, depressing a specific button or control, etc.). Once the vaporizer enters the diagnostic mode, the user takes an inhalation via the mouthpiece (the user may be instructed to do so via a signal from the device (e.g., a control light is turned on or turned to a specific color), or the user may be previously informed of the appropriate actions to take once the user enters the vaporizer into the diagnostic mode). Once a puff is taken, the microcontroller determines if both the pressure sensor and the anemometric sensing approach are providing signals to cause an increase of a temperature of the heating element. If properly functioning, the pressure sensor sends a signal to the microcontroller indicating that the pressure sensor has detected the inhalation. With the anemometric sensing approaching consistent with some implementations described herein, the microcontroller makes a determination if one or more diagnostic mode triggering criteria for a monitored parameter are met. The monitored parameter (or parameters) and the triggering criteria are similar to those described above. If the one or more diagnostic mode triggering criteria are met, this serves as an indicator of a user inhaling on the mouthpiece. If the pressure sensor does not send the signal, this may serve as an indicator that the pressure sensor is not properly functioning. The user may be alerted of this via a signal from the vaporizer (e.g., a control light is turned on or turned to a specific warning color, or the like).

As another approach in which a pressure sensor is utilized for user-suction triggered activation, the anemometric sensing approach consistent with implementations of the current subject matter can be used as a back-up for the pressure sensor. This may be implemented by monitoring one or more parameters of the heating element and determining that one or more vaporization mode triggering criteria for the parameters are met. The monitoring may be done periodically based on a predefined schedule (e.g., every 10, 20, or 30 seconds when the vaporizer is in the standby mode), continuously once the vaporizer is in the standby mode, or at another interval. In response to determining that the one or more vaporization mode triggering criteria for the parameters are met, the controller checks or measures the temperature of the heating element. The temperature reading may be obtained and/or determined after a predetermined period of time has elapsed, to give the heating element sufficient time to reach the vaporization temperature. The temperature reading may be achieved by, for example, a temperature sensor or measuring the resistance of the heating element as further described above. If the heating element is at the proper vaporization temperature, this is an indication that the pressure sensor is properly functioning and sensed the user-suction triggering activation. If, however, the heating element is not at the proper vaporization temperature, this may be an indicator that the pressure sensor is not properly functioning. In response to such a determination, a back-up heating operation may be initiated by the controller increasing the power delivery to the heating element to heat the heating element to the vaporization temperature.

In some implementations of the current subject matter, a vaporizer may include a body and a mouthpiece. Any of these devices may be configured to include cartridges including the mouthpiece, and/or heater, and/or source of vaporizable material. The controller and/or battery may be separately held within a body that mates with the cartridge. Alternatively the device may be integrated so that the heater is within the body along with the controller and other components. For example, in some variations the body may enclose a heating element, a microcontroller, and a power source. In some variations, the vaporizer may include a wick for drawing out vaporizable material from a reservoir. The vaporizer may include at least one vent for bringing air into the device and over the heating element and vaporizable material when a user takes a puff (drawing through the mouthpiece). The vaporizer may include one or more channels within the device for diverting airflow over the heating element and the vaporizable material.

Figure 8:
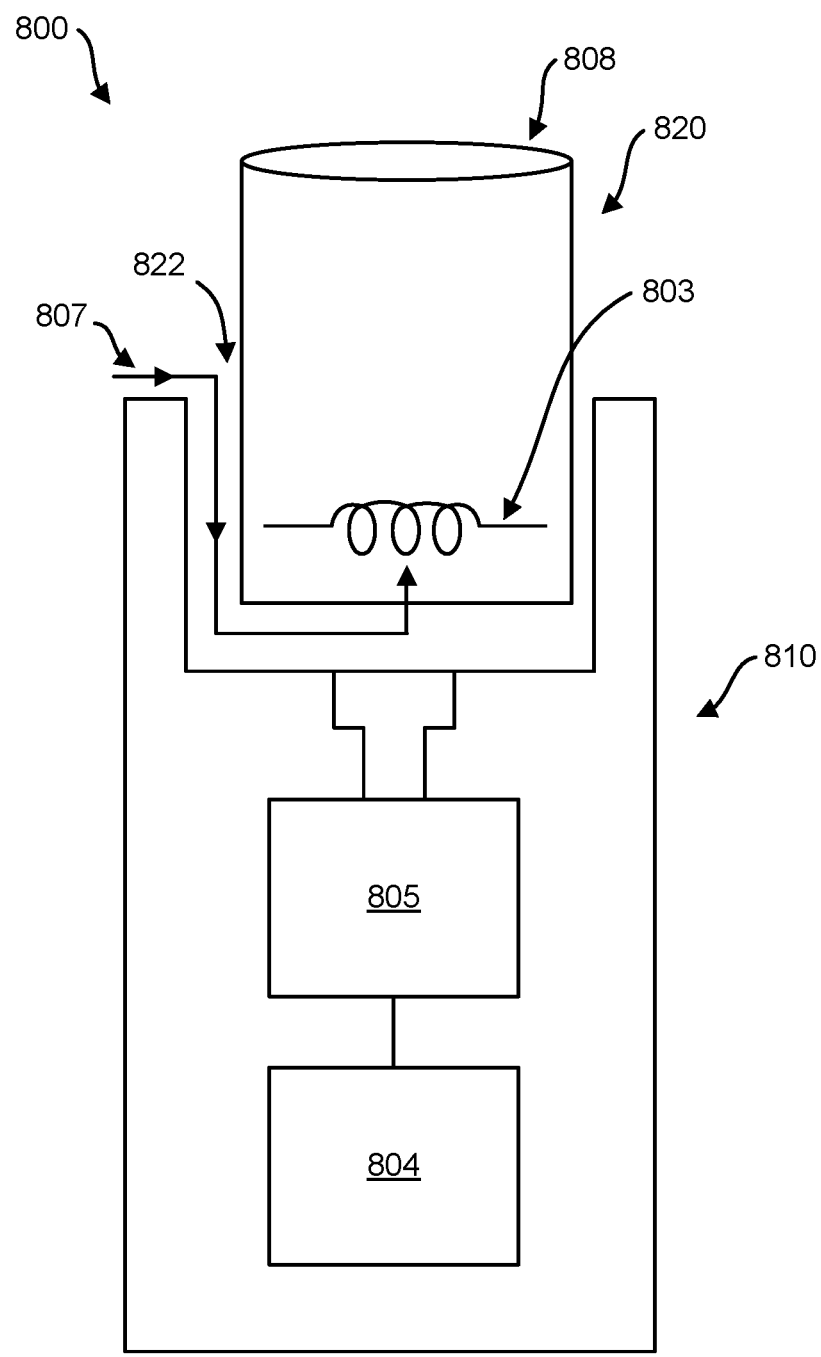
FIG. 8 illustrates features of yet another exemplary vaporizer device consistent with implementations of the current subject matter.

FIG. 8 illustrates features of an additional exemplary vaporizer device 800 consistent with implementations of the current subject matter. Vaporizer 800 includes a body 810 configured to receive a removable cartridge 820. The body 810 includes a power supply 804 that is in electrical communication with a microcontroller 805. The cartridge 820 includes a mouthpiece 808 disposed on a proximal end of the cartridge 820. A heating element 803 is contained within the cartridge 820. A defined airflow path 807 is situated in the cartridge 820 of the vaporizer 800 for ensuring that the air flow flows transversely over the heating element 803 for accurate control of the heating within the vaporizer 800. In this implementation, both an air inlet 822 and air outlet (the mouthpiece 808) are on the cartridge 820 itself, significantly simplifying the cartridge interface by eliminating airflow connections and communication between the cartridge 820 and the body 810, thus requiring only electrical contacts between the cartridge 820 and the device body 810.

Figure 9:
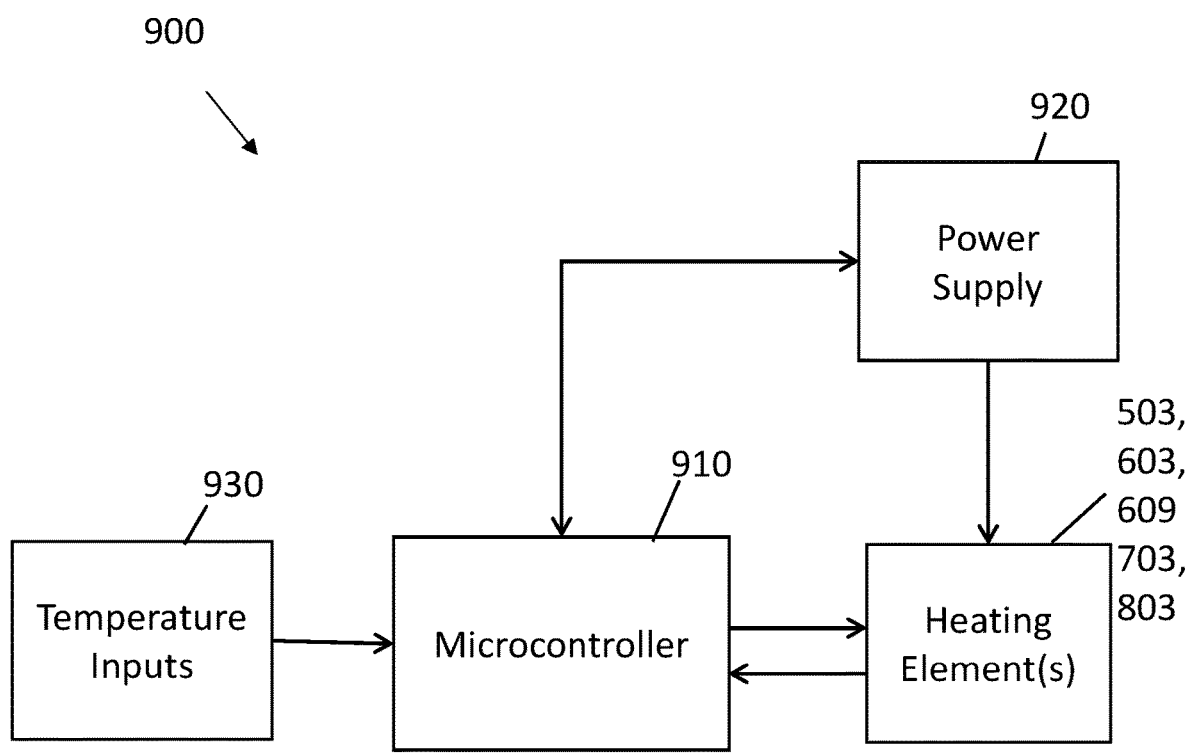
FIG. 9 illustrates features of a controller that may be adapted for regulating heat within a vaporizer device consistent with implementations of the current subject matter.

FIG. 9 illustrates features of a controller that may be adapted for regulating heat within a vaporizer device consistent with implementations of the current subject matter. Block diagram 900 includes a microcontroller 910 coupled to (e.g., in communication with, in electrical communication with, or otherwise connected) a heating element (such as the heating element 503, 603, 609, 703, 803 described above). The microcontroller 910 monitors power and/or temperature functions of the heating element as described above. An input may be a desired temperature input or inputs 930 (e.g., a desired vaporization temperature), determined and inputted by a user and used as described above by the microcontroller 910. The desired temperature input, rather than inputted by a user, may be pre-established and inputted to the microcontroller 910.

The example of FIG. 9 consistent with implementations of the current subject matter provides for delivery of electrical energy from a power source 920, that may be part of the vaporizer 500, 600, 700, 800, to the heating element 503, 603, 609, 703, 803. The power source 920 also provides power to the microcontroller 910.

Figure 10:
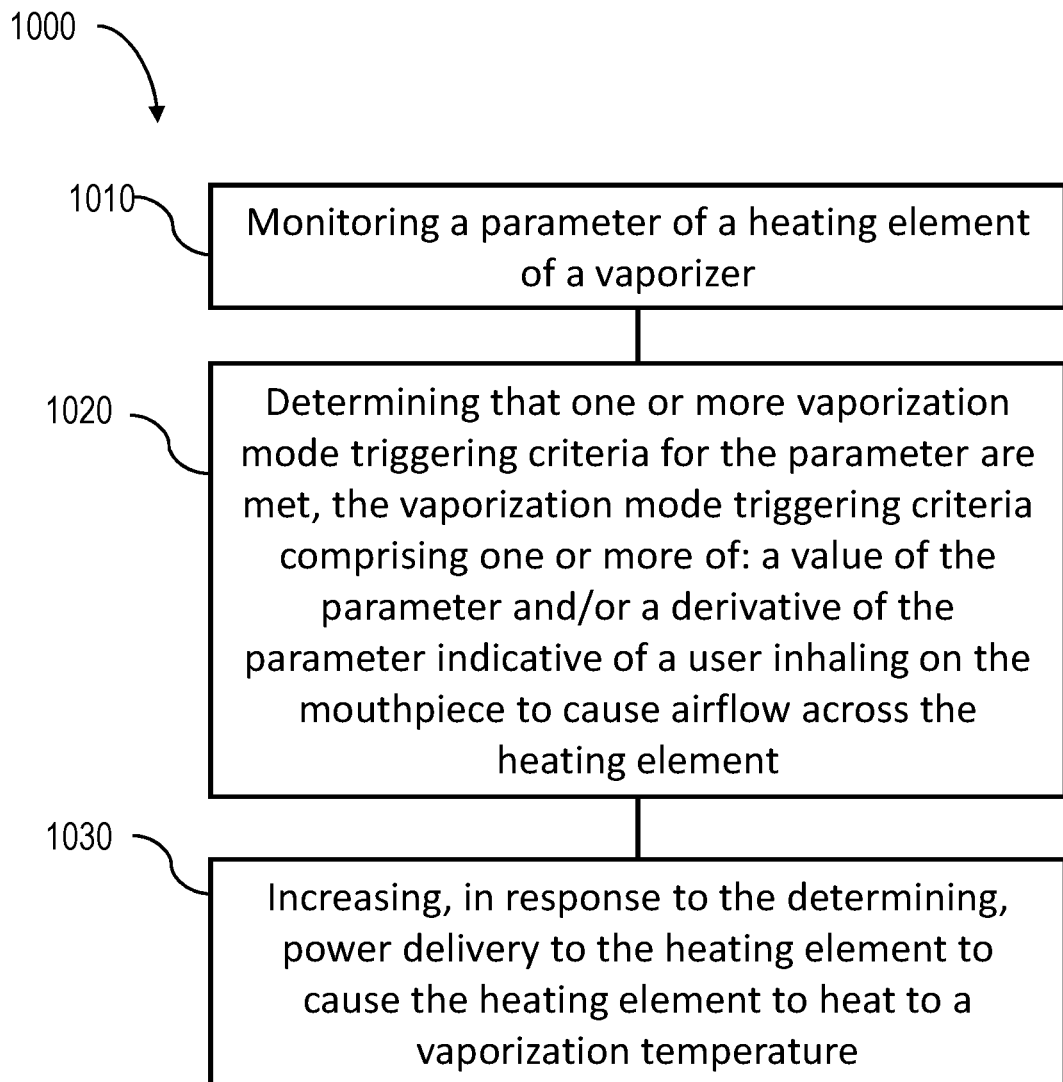
FIG. 10 shows a process flow chart illustrating features of a method of regulating heat within a vaporizer device consistent with implementations of the current subject matter.

With reference to FIG. 10, a process flow chart 1000 illustrates features of a method, which may optionally include some or all of the following. At 1010, a parameter of a heating element of a vaporizer is monitored. At 1020, a determination is made that one or more vaporization mode triggering criteria for the parameter are met. The vaporization mode triggering criteria include one or more of a value of the parameter and/or of a derivative of the parameter indicative of a user inhaling on the mouthpiece to cause airflow across the heating element. At 1030, in response to the determination related to the one or more vaporization mode triggering criteria, power delivery to the heating element is increased to cause the heating element to heat to a vaporization temperature.

Figure 11:
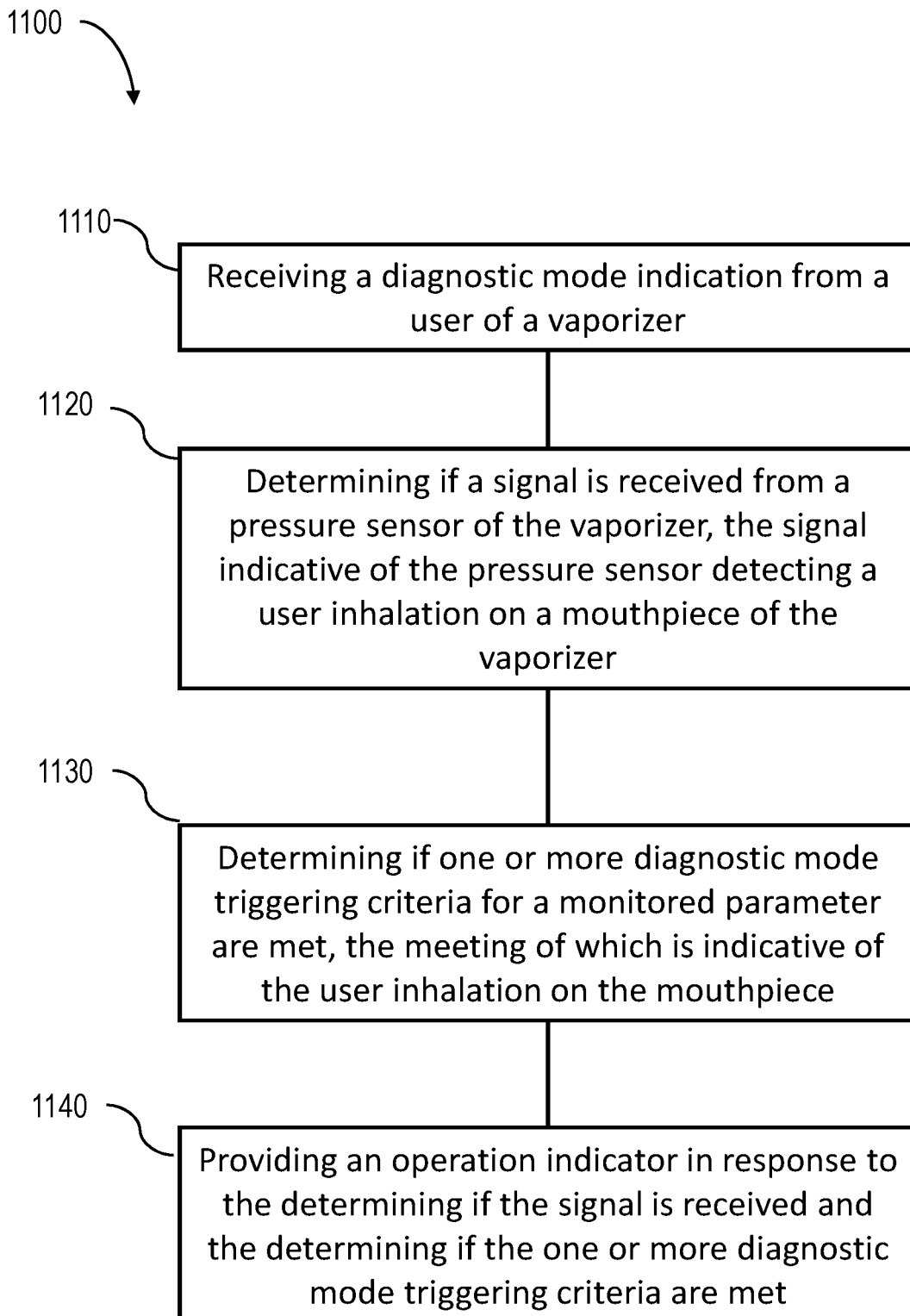
FIG. 11 shows a process flow chart illustrating additional features of a method of regulating heat within a vaporizer device consistent with implementations of the current subject matter.

With reference to FIG. 11, a process flow chart 1100 illustrates features of a method, which may optionally include some or all of the following. At 1110, a diagnostic mode indication from a user of a vaporizer may be received. At 1120, a determination is made as to whether a signal is received from a pressure sensor of the vaporizer. The signal is indicative of the pressure sensor detecting a user inhalation on a mouthpiece of the vaporizer to cause airflow of air. At 1130, a determination is made as to whether one or more diagnostic mode triggering criteria for a monitored parameter are met. If met, this is indicative of the user inhalation on the mouthpiece of the vaporizer. At 1140, an operation indicator is provided to the user in response to the determining operations. For example, the operation indicator may indicate a failed operation if the signal is not received from the pressure sensor and if the one or more diagnostic mode triggering criteria for the monitored parameter are met. If the signal is received from the pressure sensor, this is an indicator that the pressure signal is properly functioning, and an associated operation indicator (e.g., successful operation) may be provided to the user. The operation indicator may be in the form of a control light, for example.

The following descriptions of example implementations are provided for illustration of various features that may be part of the current subject matter. They are not intended to be limiting.

Described herein are vaporizer apparatuses (e.g., devices, systems, and components) and methods for regulating heating within a vaporizer by sensing flow over a resistive heater by monitoring the power (e.g., current, voltage, or some combination of the two) required to maintain or achieve a temperature of the resistive heater or these apparatuses may monitor the temperature of the resistive heater when the applied power is kept at a predetermined level. For example, the apparatus and methods described herein may compare the absolute power applied to achieve a target temperature to a threshold power value, and/or may compare the rate of change of the temperature when a predetermined power is applied. In particular, the vaporization apparatuses and methods described herein may use the same heating element (e.g., resistive heater) that vaporizes the vaporizable material as the flow sensor (e.g., as an anemometer flow sensor) by monitoring the power applied to the heating element.

For example, a vaporizer may include one or more heating elements (resistive heaters) that are used for vaporizing a vaporizable material and may also be directly monitored, e.g., using a controller and/or other monitoring circuitry, to monitor the temperature and applied power necessary to heat the heating element and to compare the applied power and temperature to a predetermined value (threshold). In this way, as will be described in greater detail herein, the apparatus may detect airflow over the heating element when a user inhales through the mouthpiece of the vaporizer to cause flow of air over the heating element.

For example, the apparatus may be placed in an 'on' state (e.g., turned on), either automatically (by sensing a user holding the device, and/or by sensing a lip or hand contacting the device, including the mouthpiece) or manually (e.g., by toggling a control such as a switch, button, etc.). In the on state the apparatus may maintain the heating element (resistive heater) at a predetermined temperature, referred to herein as a base temperature or standby temperature (e.g., between 40-80° C., between 45-75° C., between 50-70° C., etc.). The apparatus may then monitor the applied power to detect when the applied power reaches or exceeds a threshold indicating airflow from a user drawing air (inhaling) across the heating element. Alternatively, a predetermined power (a base or standby power level) may be applied and the temperature monitored to determine when the temperature reaches or goes below a threshold triggering temperature (which may be, for example, between 40° C. and 70° C.), indicating a user drawing air through the apparatus. As used herein the term 'power' may refer to current, voltage, or a combination of current and voltage (e.g., current time voltage).

In general, the apparatuses and methods described herein are configured to operate with vaporizers in which the temperature of the heating element (e.g., resistive heater) may be determined and used as part of a feedback control for the temperature (e.g., a PID, proportional-integral-derivative, controller). For example, the controller (e.g., microcontroller on a PCB) may be configured to monitor the temperature of the heater such that the vaporizable material is heated to a prescribed temperature. The prescribed temperature may be an input provided by the user. A temperature sensor may be in communication with the microcontroller to provide an input temperature to the microcontroller for temperature regulation. A temperature sensor may be a thermistor, thermocouple, thermometer, or any other temperature sensors. Alternatively or additionally, the temperature of the heating element (resistive heater) may be determined by the resistance of the heating element (without the need for a separate additional temperature sensor). In any of the variations described herein, resistance of the heating element (e.g., resistive heater) may be used in place of temperature, or the resistance value may be converted to a temperature, in variations in which the resistance of the resistive heater is characteristic of the temperature of the resistive heater. For example, the target resistance may be estimated based on the electrical properties of the resistive heater, e.g., the temperature coefficient of resistance or TCR, of the resistive heater (e.g., "resistive heating element" or "vaporizing element"). As is known in the art, the resistance of the heater may be used to calculate the temperature of the heater (particularly in comparison to a reference resistance value). Thus, the resistance of the heating element may be an input to the controller both to control the temperature and to determine flow. In some cases, the resistance may be determined by the controller (e.g., microcontroller) based on a measurement from a circuit with a resistor with at least one known resistance, for example, a Wheatstone bridge. Alternatively, the resistance of the heating element may be measured with a resistive voltage divider in contact with the heating element and a resistor with a known and substantially constant resistance. The measurement of the resistance of the heating element (or the difference to known resistance) may be amplified by an amplifier. The amplifier may be a standard op amp or instrumentation amplifier. The amplified signal may be substantially free of noise. In some cases, a charge time for a voltage divider between the heating element and a capacitor may be determined to calculate the resistance of the heating element. In some cases, the microcontroller must deactivate the heating element during resistance measurements. The resistance of the heating element may be a function of the temperature of the heating element such that the temperature may be directly determined from resistance measurements. Determining the temperature directly from the heating element resistance measurement rather than from an additional temperature sensor may generate a more accurate measurement because unknown contact thermal resistance between the temperature sensor and the heating element is eliminated. Additionally, the temperature measurement may be determined directly and therefore faster and without a time lag associated with attaining equilibrium between the heating element and a temperature sensor in contact with the heating element.

In the apparatuses and methods described herein, draw (inhalation) may be detected when the device is on, and a heating element is maintained a base temperature by detecting when the power required to maintain the base temperature (or base resistance of the resistive heater, when the resistance value is used to control the heater temperature) increases above a power threshold, e.g., greater than 2% of the steady-state power (e.g., greater than 5%, greater than 7%, greater than 10%, greater than 12%, greater than 15%, etc.). The steady state power may be predetermined for the heater apparatus for the basal power, or it may be determined empirically from operation of the apparatus, or some combination thereof. Equivalently, draw from the mouthpiece of the apparatus may be detected when the heating element is held at a fixed (basal) power and the temperature decreases below a threshold, e.g., decreases by 1% or more of steady-state temperature (e.g., decreases by 2% or more, 5% or more, 7% or more, 10%, or more, 15% or more, etc.). As mentioned, in some cases the resistance (when the resistance is proportional to the temperature of the heating element) may be used more simply instead of temperature, so that draw may be determined when the resistance of the heating element when held at a base power decreases below a threshold.

In general, the vaporizers described herein may include a body and a mouthpiece. Any of these devices may be configured to include cartridges including the mouthpiece, and/or resistive heater, and/or source of vaporizable material; the controller and/or battery may be separately held within a body that mates with the cartridge. Alternatively the apparatus may be integrated so that the resistive heater is within the body along with the controller and other components. For example, in some variations the body may enclose: a heating element, a microcontroller and a power source. In some variations, the vaporizer may include a wick for drawing out vaporizable material from a reservoir. The vaporizer may include at least one vent for bringing air into the device and over the heating element and vaporizable material when a user takes a puff (drawing through the mouthpiece). The vaporizer may include one or more channels within the device for diverting airflow over the heating element (e.g., resistive heater, such as a resistive coil) and the vaporizable material.

Any of the vaporizers described herein may have different states. For example, a vaporizer may be in an OFF state until the user turns it on manually or automatically (by touching it to the lips, etc.). The device may be manually turned on by the user pressing the ON/OFF switch. Once the vaporization apparatus is in the ON state, the controller (e.g., a microcontroller within the body of the apparatus) may control the power supply to deliver power to the heating element to reach a base (also referred to as "standby") temperature, where the standby temperature is well below a vaporization temperature of the target vaporizable material, and monitor the power applied (e.g., current, voltage, etc.). Alternatively, the apparatus may be configured to apply a base (e.g., standby) power on the heater and monitor the temperature (or resistance) of the heater.

For example, the microcontroller may be programmed to hold the base temperature by varying the amount of power being sent to the heating element. When a user takes a puff on the mouthpiece of the vaporization apparatus, air is drawn into the vaporizer and passes over the heating element where the air cools the heating element by some amount. The processor may detect this cooling and my either increase the power applied (via a control loop) to maintain the temperature, or it may detect the drop in temperature (e.g., or corresponding change in resistance) when the power is held constant. In the first instance, when the apparatus is controlled to maintain a base temperature, the power drawn to compensate for the temperature deviation between the heating element and the standby temperature meets or exceeds a pre-determined power value (threshold), the controller may recognize that this may be a user taking a puff and initiates (trigger) an increase in power applied to the heating element so that the heating element may reach the target vaporization temperature (typically between 100 and 400° C.). The microcontroller may initiate a cool off mode when the amount of power needed to maintain the vaporization temperature fall below a second pre-set power level.

In any of these variations draw may be determined based on the rate of change or acceleration (first or second derivative) of the value (power, temperature, resistance, etc.) rather than the magnitude of the value. In particular, when draw may be detected even when increasing the temperature from a standby temperature to vaporization temperature by comparing the rate of change (or acceleration) of the energy applied, resistance or temperature to a threshold value. For example, if the rate of change of the temperature when increasing the temperature from the resting (standby) temperature, in the standby mode, to the vaporizing temperature, in the vaporizing or heating mode, is slower than a threshold rate value, then the user may be continuing to draw on the mouthpiece; alternatively if the rate of change is greater than or equal to a threshold value then the user may have stopped puffing, and the controller may return the temperature back to a standby value. Once the apparatus is at temperature (at vaporization temperature) in the vaporization mode, the controller may compare the energy applied to maintain the vaporization temperature to a second threshold value to determine when the user has stopped puffing, so that the temperature may be returned to a standby level (e.g., when the power necessary to keep the temperature at the vaporization temperature falls below a threshold).

For example, the controller may be programmed to detect a rate of change in either the power needed to maintain a temperature at the heating element or the rate of temperature change of the heating element and correlate the change with when the user is taking a puff or not. When the user is taking a puff, the rate of change in the power needed to maintain the standby temperature or rate of change in temperature increases. When the microcontroller detects a rate change above a threshold value, then it may initiate bringing the heating element to the vaporization temperature. When the rate of change in either the power needed to maintain the vaporization temperature or the temperature drops below a threshold, the microcontroller may associate that with a user stopping the puff and bring the heating element temperature back to the standby temperature.

As mentioned, flow in the standby state may alternatively be detected by the apparatus when holding the power supplied to the heating element constant while allowing the standby temperature to fluctuate. Once a user takes a puff on the vaporization apparatus, the temperature at the heating element will drop and when the temperature falls below a threshold temperature value the controller may recognize that the user is taking a puff and trigger the heating to the vaporization temperature.

In some aspects of the invention, the vaporization apparatus may include a second coil that functions to correlate the air flow passing over it with either a temperature change or a power change. In this variation, the second coil may be placed downstream of the primary heating coil and away from moisture and/or vapors generated. The second coil is in electrical communication with the microcontroller and the power supply.

The apparatuses described herein may include an oven for vaporizing a solid material. The oven is in thermal contact with a heating element. The heating element temperature is controlled in the same manner as the heating element in vaporization apparatuses having a wick.

The apparatuses described herein may include capacitive sensing for controlling or aid with controlling the vaporization heating mechanism. The capacitive sensing may be configured to sense whether a user's lips are in contact with the mouthpiece which may indicate the user's intention to use the vaporization apparatus.

The apparatuses described herein may include an accelerometer. The accelerometer may be programmed to sense certain types of motions that may be used singly or in conjunction with the anemometric-assisted control for regulating heating within the vaporization apparatus.

Thus, described herein are methods of controlling vaporizers, including method of controlling a vaporization apparatus having a resistive heater configured to vaporize a vaporizable material and detect a user inhaling on the vaporization apparatus, the method comprising: maintaining a base temperature on a resistive heater by applying power to the resistive heater when the vaporization apparatus is on; monitoring the power necessary to maintain the base temperature of the resistive heater; increasing the temperature of the resistive heater from the base temperature to a vaporizing temperature when the power necessary to maintain the base temperature meets or exceeds a first power threshold; and vaporizing the vaporizable material in communication with the resistive heater.

Any of these methods may also include reducing the temperature back to the base temperature once the power necessary to maintain the vaporization temperature has decreased to or below a second power threshold.

In general, monitoring the power necessary may include monitoring one of the voltage or current applied to the resistive heater. Increasing the temperature may comprise increasing the power applied to the resistive heater.

Any of these methods may also include reducing the temperature down to the base temperature when the rate of change of the power applied to increase the temperature of the resistive heater to the vaporizing temperature falls below a rate of change threshold.

Any of the methods described herein may include turning on a power on the vaporization apparatus. For example, these methods may include automatically turning on power to the vaporization apparatus by capacitively sensing a user touching the device, automatically turning on power to the vaporization apparatus when an accelerometer device detects movement of the vaporization apparatus, etc.

Monitoring the power necessary to maintain the base temperature may include monitoring the rate of change of the power.

Also described herein are apparatus in which the same structure (the heater) is used both for vaporizing the material and for detecting flow (e.g., the heater is configured as an anemometer). For example, described herein are vaporization apparatuses configured to detect a user inhaling on the vaporization apparatus using a resistive heater configured to vaporize a vaporizable material, the apparatuses comprising: the resistive heater; a mouthpiece; a controller configured to maintain the resistive heater at a base temperature and to monitoring the power necessary to maintain the base temperature of the resistive heater, the controller further configured to increase the temperature of the resistive heater to a vaporization temperature when the power necessary to maintain the base temperature meets or exceeds a first power threshold; a source of vaporizable material in communication with the resistive heater; and a power source configured to power the controller and the resistive heating element.

The controller may be further configured to reduce the temperature back to the base temperature once the power necessary to maintain the vaporization temperature has decreased to or below a second power threshold. The controller may be further configured to monitor one of the voltage or current applied to the resistive heater.

As mentioned, any of these apparatuses may include an ON/OFF switch, wherein the controller is configured to maintain the base temperature when the ON/OFF switch is on. The apparatus may include a capacitive sensor configured to automatically turn the vaporization apparatus on and to maintain the base temperature when a user contacts the vaporization apparatus. Alternatively or additionally, the apparatus may include an accelerometer configured to automatically turn the vaporization apparatus on and to maintain the base temperature when the vaporization apparatus is moved.

In variations having a base temperature, the base temperature may be, e.g., between about 50 and 70 degrees Celsius. In variations having a base power, the base power may be chosen such that the normal running temperature of the heater at the base power is between this temperature range.

The resistive heater may be a resistive coil (e.g., a coil wound around a wick or oven). Thus, in some variations, the apparatus includes a wick in thermal communication with the resistive heater.

In general, the source of vaporizable material may comprise a reservoir for holding the vaporizable material (e.g., tank, etc.).

The vaporization apparatus may include an oven for vaporizing a solid vaporizable material wherein the oven is in thermal communication with the resistive heater.

As mentioned, any of the apparatuses described herein may include a removable cartridge that couples to a (reusable) base. For example, the resistive heater, mouthpiece, and source of vaporizable material may be part of a removable cartridge in electrical contact with the power supply and controller.

Also described herein are apparatuses in which a second resistive heater is used in-line with the resistive heater that vaporizes material. The second resistive heater may not directly contact vaporizable material, but may be positioned in the flow path of the (first) resistive heater that vaporizes the material. For example, a vaporization apparatus may include: a mouthpiece; an air path extending from the mouthpiece; a first resistive heater in the air path; a second resistive heater configured to measure air flow through the air path, wherein the second resistive heater is within the air path; a controller configured to maintain a base temperature on the second resistive heater and to increase the temperature of the first resistive heater to a vaporization temperature when the power necessary to maintain the base temperature of the second resistive heater exceeds a first power threshold; a source of vaporizable material in communication with the first resistive heater; and a power supply.

The second resistive heater may be a coil (e.g., resistive coil) or other wire element. The vaporization apparatus may include a wick in communication with the coil. The source may comprise a reservoir for holding the vaporizable material.

The first resistive heater (e.g., configured to vaporize the material) may be between the second resistive heater and the mouthpiece. Alternatively, the second resistive heater (which is not configured to vaporize the material) may be between the first resistive heater and the mouthpiece.

As mentioned, the apparatus may include a removable cartridge including the mouthpiece and other components. For example, the mouthpiece, air path, first resistive heater, second resistive heater and source of vaporizable material may all be part of a removable cartridge in electrical contact with the power supply and controller.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A vaporizer comprising:
   a heating element configured to generate heat to vaporize a vaporizable material;
   a mouthpiece connected by a flow path to the heating element; and
   a controller coupled to the heating element and configured to perform operations comprising:
      monitoring a parameter of the heating element;
      determining that one or more vaporization mode triggering criteria for the parameter are met, the vaporization mode triggering criteria comprising one or more of: a value of the parameter and/or of a derivative of the parameter indicative of a user inhaling on the mouthpiece to cause airflow across the heating element;
      increasing, in response to the determining, power delivery to the heating element to cause the heating element to heat to a vaporization temperatures;
      determining that one or more standby mode triggering criteria for the parameter are met, the standby mode triggering criteria comprising one or more of: a second value of the parameter and/or of the derivative of the parameter indicative of airflow across the heating element stopping due to a user no longer inhaling on the mouthpiece; and
      decreasing, in response to the determination that one or more standby mode triggering criteria for the parameter are met, power delivery to the heating element to cause the heating element heat to cool to a standby temperature.

2. The vaporizer of claim 1, wherein the monitoring is performed while the heating element is maintained at a standby temperature.

3. A method comprising:
   monitoring, by a controller, a parameter of a heating element of a vaporizer, the controller coupled to the heating element, the heating element configured to generate heat to vaporize a vaporizable material, and the vaporizer comprising a mouthpiece connected by a flow path to the heating element;
   determining, by the controller, that one or more vaporization mode triggering criteria for the parameter are met, the vaporization mode triggering criteria comprising one or more of: a value of the parameter and/or of a derivative of the parameter indicative of a user inhaling on the mouthpiece to cause airflow across the heating element;
   increasing, by the controller, in response to the determining, power delivery to the heating element to cause the heating element to heat to a vaporization temperature;
   determining, by the controller, that one or more standby mode triggering criteria for the parameter are met, the standby mode triggering criteria comprising one or more of: a second value of the parameter and/or of the derivative of the parameter indicative of airflow across the heating element stopping due to a user no longer inhaling on the mouthpiece; and
   decreasing, by the controller, in response to the determination that one or more standby mode triggering criteria for the parameter are met, power delivery to the heating element to cause the heating element heat to cool to a standby temperature.

4. The vaporizer of claim 1, wherein the operations further comprise detecting an on condition of the vaporizer and, in response to the detecting, providing power to the heating element to cause the heating element to reach the standby temperature.

5. The vaporizer of claim 1, wherein the parameter comprises at least one of: a temperature, a power delivery, a resistance, a voltage, and a current of the heating element.

6. The vaporizer of claim 1, wherein the parameter comprises a power delivered to the heating element while maintaining a setpoint temperature, and the vaporization mode triggering criteria comprise a value of at least one of: the power delivered, a first derivative of the power delivered, and a second derivative of the power delivered.

7. The vaporizer of claim 1, wherein the parameter comprises a temperature measured while maintaining a power delivery to the heating element, and the vaporization mode triggering criteria comprise a value of: at least one of the temperature, a first derivative of the temperature, and a second derivative of the temperature.

8. The vaporizer of claim 1, further comprising a capacitive sensor configured to cause the vaporizer to automatically turn on upon detecting user contact with the mouthpiece.

9. The vaporizer of claim 1, further comprising an accelerometer configured to cause the vaporizer to automatically turn on upon detecting a motion or a combination of motions of the vaporizer.

10. The vaporizer of claim 1, wherein the heating element comprises a coil.

11. The vaporizer of claim 1, further comprising:
    a wick configured to be heated by the heating element; and
    a liquid source of the vaporizable material in fluid communication with the wick.

12. The vaporizer of claim 1, further comprising a source of the vaporizable material.

13. The vaporizer of claim 12, wherein the source of the vaporizable material comprises an oven for the holding the vaporizable material.

14. The vaporizer of claim 12, wherein the heating element, the mouthpiece, and the source of the vaporizable material are part of a removable cartridge in electrical contact with the controller, wherein at least part of the flow path is within the cartridge.

15. The vaporizer of claim 14, wherein the source of the vaporizable material comprises a reservoir for holding the vaporizable material.

16. The vaporizer of claim 1, further comprising a power supply configured to power the controller and the heating element.

17. A vaporizer comprising:
    a removable cartridge comprising:
       a heating element configured to generate heat to vaporize a vaporizable material;
       a source of the vaporizable material;
       a flow path for air to flow;
       a mouthpiece connected by the flow path to the heating element; and
    a body configured to receive the removable cartridge, the body comprising:
       a controller coupled to the heating element when the body receives the removable cartridge, the controller configured to perform operations comprising:
          monitoring a parameter of the heating element;
          determining that one or more vaporization mode triggering criteria for the parameter are met, the vaporization mode triggering criteria comprising one or more of: a value of the parameter and/or of a derivative of the parameter indicative of a user inhaling on the mouthpiece to cause airflow across the heating element; and increasing, in response to the determining, power delivery to the heating element to cause the heating element to heat to a vaporization temperature.

18. The method of claim 3, wherein the monitoring is performed while the heating element is maintained at a standby temperature.

19. The vaporizer of claim 17, wherein the monitoring is performed while the heating element is maintained at a standby temperature.

20. The method of claim 3, further comprising detecting, by the controller, an on condition of the vaporizer and, in response to the detecting, providing, by the controller, power to the heating element to cause the heating element to reach the standby temperature.

21. The method of claim 3, wherein the parameter comprises at least one of: a temperature, a power delivery, a resistance, a voltage, and a current of the heating element.

22. The method of claim 3, wherein the parameter comprises a power delivered to the heating element while maintaining a setpoint temperature, and the vaporization mode triggering criteria comprise a value of at least one of: the power delivered, a first derivative of the power delivered, and a second derivative of the power delivered.

23. The method of claim 3, wherein the parameter comprises a temperature measured while maintaining a power delivery to the heating element, and the vaporization mode triggering criteria comprise a value of: at least one of the temperature, a first derivative of the temperature, and a second derivative of the temperature.

24. The method of claim 3, wherein the vaporizer further comprises a capacitive sensor configured to cause the vaporizer to automatically turn on upon detecting user contact with the mouthpiece.

25. The method of claim 3, wherein the vaporizer further comprises an accelerometer configured to cause the vaporizer to automatically turn on upon detecting a motion or a combination of motions of the vaporizer.

26. The method of claim 3, wherein the heating element comprises a coil.

27. The method of claim 3, wherein the vaporizer further comprises:
a wick configured to be heated by the heating element; and
a liquid source of the vaporizable material in fluid communication with the wick.

28. The method of claim 3, wherein the vaporizer further comprises a source of the vaporizable material.

29. The method of claim 28, wherein the source of the vaporizable material comprises an oven for the holding the vaporizable material.

30. The method of claim 28, wherein the heating element, the mouthpiece, and the source of the vaporizable material are part of a removable cartridge in electrical contact with the controller, wherein at least part of the flow path is within the cartridge.

31. The method of claim 30, wherein the source of the vaporizable material comprises a reservoir for holding the vaporizable material.

32. The method of claim 3, wherein the vaporizer further comprises a power supply configured to power the controller and the heating element.

33. The vaporizer of claim 17, wherein the operations further comprise:
determining that one or more standby mode triggering criteria for the parameter are met, the standby mode triggering criteria comprising one or more of: a second value of the parameter and/or of the derivative of the parameter indicative of airflow across the heating element stopping due to a user no longer inhaling on the mouthpiece; and
decreasing, in response to the determining, power delivery to the heating element to cause the heating element heat to cool to a standby temperature.

34. The vaporizer of claim 33, wherein the operations further comprise detecting an on condition of the vaporizer and, in response to the detecting, providing power to the heating element to cause the heating element to reach the standby temperature.

35. The vaporizer of claim 17, wherein the parameter comprises at least one of: a temperature, a power delivery, a resistance, a voltage, and a current of the heating element.

36. The vaporizer of claim 17, wherein the parameter comprises a power delivered to the heating element while maintaining a setpoint temperature, and the vaporization mode triggering criteria comprise a value of at least one of: the power delivered, a first derivative of the power delivered, and a second derivative of the power delivered.

37. The vaporizer of claim 17, wherein the parameter comprises a temperature measured while maintaining a power delivery to the heating element, and the vaporization mode triggering criteria comprise a value of: at least one of the temperature, a first derivative of the temperature, and a second derivative of the temperature.

38. The vaporizer of claim 17, further comprising a capacitive sensor configured to cause the vaporizer to automatically turn on upon detecting user contact with the mouthpiece.

39. The vaporizer of claim 17, further comprising an accelerometer configured to cause the vaporizer to automatically turn on upon detecting a motion or a combination of motions of the vaporizer.

40. The vaporizer of claim 17, wherein the heating element comprises a coil.

41. The vaporizer of claim 17, further comprising:
a wick configured to be heated by the heating element; and
wherein the source of the vaporizable material is a liquid source in fluid communication with the wick.

42. The vaporizer of claim 17, wherein the source of the vaporizable material comprises a reservoir for holding the vaporizable material.

43. The vaporizer of claim 17, further comprising a power supply configured to power the controller and the heating element.

* * * * *